(12) United States Patent
Schammel et al.

(10) Patent No.: US 8,163,954 B2
(45) Date of Patent: *Apr. 24, 2012

(54) PROCESS AND CATALYST FOR OXIDIZING AROMATIC COMPOUNDS

(75) Inventors: Wayne P. Schammel, Plainfield, IL (US); Victor Adamian, Naperville, IL (US); Stephen P. Brugge, Naperville, IL (US); William H. Gong, Elmhurst, IL (US); Peter D. Metelski, Bolingbrook, IL (US); Philip O. Nubel, Naperville, IL (US); Chengxiang Zhou, Lisle, IL (US)

(73) Assignee: BP Corporation North America Inc., Houston, TX (US)

( * ) Notice: Subject to any disclaimer, the term of this patent is extended or adjusted under 35 U.S.C. 154(b) by 419 days.

This patent is subject to a terminal disclaimer.

(21) Appl. No.: 12/298,554

(22) PCT Filed: May 4, 2007

(86) PCT No.: PCT/US2007/068274
§ 371 (c)(1),
(2), (4) Date: Oct. 27, 2008

(87) PCT Pub. No.: WO2007/133978
PCT Pub. Date: Nov. 22, 2007

(65) Prior Publication Data
US 2009/0088585 A1    Apr. 2, 2009

Related U.S. Application Data

(60) Provisional application No. 60/798,781, filed on May 8, 2006.

(51) Int. Cl.
*C07C 51/16* (2006.01)
(52) U.S. Cl. ........ 562/417; 562/405; 562/407; 562/408; 562/409; 562/412
(58) Field of Classification Search .................. None
See application file for complete search history.

(56) References Cited

U.S. PATENT DOCUMENTS

| | | | | |
|---|---|---|---|---|
| 3,845,117 A | 10/1974 | Kollar | | 260/524 |
| 3,865,870 A | 2/1975 | Cronauer et al. | | 260/524 |
| 4,334,086 A | 6/1982 | Hanotier et al. | | 562/413 |
| 4,465,633 A | 8/1984 | Goel et al. | | 260/410 |
| 5,189,006 A | 2/1993 | Augustine et al. | | 502/339 |
| 5,280,001 A | 1/1994 | Tso et al. | | 502/170 |
| 5,864,051 A * | 1/1999 | Iwasawa et al. | | 568/479 |
| 6,160,159 A | 12/2000 | Smith | | 560/77 |
| 6,160,170 A * | 12/2000 | Codignola | | 562/413 |
| 6,528,683 B1 | 3/2003 | Heidemann et al. | | 562/542 |

FOREIGN PATENT DOCUMENTS

| | | |
|---|---|---|
| CN | 1168131 A | 12/1997 |
| CN | 1304336 A | 7/2001 |
| CN | 1314878 A | 9/2001 |
| DE | 10 2004002262 | 1/2004 |
| EP | 0965383 | 6/1999 |
| WO | WO 02103693 | 12/2002 |
| WO | WO 2005066107 | 7/2005 |
| WO | WO 2006103693 | 11/2005 |
| WO | WO 2007133973 | 11/2007 |
| WO | WO 2007133976 | 11/2007 |

OTHER PUBLICATIONS

Yang, Advances In The Catalytic Systems For Synthesis Of Terephthalic Acid Via Oxidation Of Paraxylene, Industrial Catalysts, vol. 12, No. 6, Jun. 2004, pp. 28-29.
Benazzi et al,—Heterogeneous Catalyzed Benzylic Acetoxylation of Methylated Aromatic Hydrocarbons, Journal of Catalysts 140 pp. 311-327 (1993).
Benazzi et al.—Palladium-Catalyzed Benzylic Acetoxylation of Toluene, Journal of Molecular Catalysts 69, pp. 299-321 (1991).
Partenheimer—Methodology and Scope of Metal/Bromide Autoxidation of Hydrocarbons, Elsevier pp. 69-158 (1995).

* cited by examiner

*Primary Examiner* — Sudhakar Katakam
(74) *Attorney, Agent, or Firm* — Stephen L. Hensley

(57) ABSTRACT

Catalytic compositions for conversion of substituted aromatic feed materials to oxidized products comprising aromatic carboxylic acid derivatives of the substituted aromatic feed materials comprise a combination comprising a palladium component, an antimony component and/or a bismuth component, and one or more Group 4, 5, 6 or 14 metal or metalloid components. A process for oxidizing substituted aromatic feed materials comprises contacting the feed material with oxygen in the presence of such a catalytic composition in a liquid reaction mixture.

19 Claims, No Drawings

PROCESS AND CATALYST FOR OXIDIZING AROMATIC COMPOUNDS

This application claims the benefit of U.S. Provisional Application No. 60/798,781 filed May 8, 2006, the disclosure of which is incorporated herein by reference.

FIELD OF THE INVENTION

This invention relates to a process for converting substituted aromatic compounds to oxidized products comprising aromatic carboxylic acids and a catalyst composition useful for such a process. More particularly, the invention relates to catalytic oxidation of feedstock materials comprising aromatic hydrocarbons having oxidizable substituent groups to an oxidized product comprising aromatic carboxylic acid in a liquid reaction mixture using a catalyst composition that is active for such oxidation in the absence of bromine sources commonly used to promote catalytic oxidation of substituted aromatic compounds to aromatic carboxylic acids and comprises a palladium component, a Group 15 metal or metalloid component selected from antimony, bismuth or a combination thereof and a Group 4, 5, 6 or 14 metal or metalloid component.

BACKGROUND OF THE INVENTION

Terephthalic acid and other aromatic carboxylic acids are widely used in the manufacture of polyesters, commonly by reaction with one or more glycols, and particularly ethylene glycol and combinations thereof with one or more higher homologues of alkylene glycols, for conversion to fiber, film, containers, bottles and other packaging materials, and molded articles.

In commercial practice, aromatic carboxylic acids are commonly made by liquid phase oxidation in an aqueous acetic acid solvent of methyl-substituted benzene and naphthalene feedstocks, in which the positions of the methyl substituents correspond to the positions of carboxyl groups in the desired aromatic carboxylic acid product. Oxidation is conducted by contacting the feedstock with air or another source of oxygen, which is normally gaseous, in the presence of a catalyst comprising cobalt and manganese promoted with a source of reactive bromine as described in U.S. Pat. No. 2,833,816. The oxidation is exothermic and yields the aromatic carboxylic acid together with by-products, including partial and intermediate oxidation products of the aromatic feedstock as well as oxidation and other reaction products of the acetic acid solvent such as methanol, methyl acetate, methyl bromide, carbon monoxide and carbon dioxide. Water is also generated as a by-product. The aromatic carboxylic acid oxidation product, by-products and intermediate oxidation products of the feedstock are commonly formed dissolved or as solids suspended in the liquid phase reaction mixture and are commonly recovered by crystallization and solid-liquid separation techniques.

Pure forms of aromatic carboxylic acids are often favored for manufacture of polyesters for important applications, such as fibers, bottles, and other containers and packaging materials, because impurities, such as by-products generated from aromatic feedstocks in oxidation processes such as those described above and, more generally, various carbonyl-substituted aromatic species, are known to cause or correlate with color formation in polyesters made from the carboxylic acids and, in turn, off-color in polyester converted products. Aromatic carboxylic acids with reduced levels of impurities can be made by further oxidizing crude products from liquid phase oxidation as described above, for example at one or more progressively lower temperatures and/or oxygen levels or during crystallization steps commonly used to recover products of the oxidation, for conversion of feedstock partial oxidation products to the desired acid product, as known from U.S. Pat. Nos. 4,877,900, 4,772,748 and 4,286,101. Preferred pure forms of terephthalic acid and other aromatic carboxylic acids with lower impurities contents, such as purified terephthalic acid or "PTA", are made by catalytically hydrogenating less pure forms of the acids, such as crude product comprising aromatic carboxylic acid and by-products generated by liquid phase oxidation of aromatic feedstock, so-called medium purity products or other impure forms of the acids, in solution at elevated temperature and pressure using a noble metal catalyst. In some commercial operations, liquid phase oxidation of alkyl aromatic feed materials to crude aromatic carboxylic acid and purification of the crude product are often conducted in continuous integrated processes in which crude product from liquid phase oxidation is used as starting material for purification.

A difficulty in manufacture of aromatic carboxylic acids by such processes results from use of bromine-promoted oxidation catalysts. Bromine sources used with the catalyst and reaction products thereof formed during oxidation are corrosive. To limit corrosion, process equipment, including major equipment items such as oxidation reactors and off-gas treatment equipment, is normally constructed using titanium or other expensive, corrosion-resistant metals or alloys. Treatment of process off-gases to avoid atmospheric emissions of volatile bromine compounds formed in the process, such as by thermal or catalytic oxidations to oxidize organic bromine compounds to carbon oxides and molecular bromine and reduction of the latter to anionic bromine using sodium formate, also are commonly used, adding complexity and cost to manufacturing processes.

Eliminating bromine from conventional cobalt-manganese oxidation catalysts is not practical for commercial scale aromatic carboxylic acid manufacture because yields of desired products are unacceptably low. In addition, oxidation of acetic acid solvent for the liquid phase reaction tends to increase in cobalt and manganese-catalyzed oxidations without bromine. Sacrificial promoters, such as methyl ethyl ketone and acetaldehyde, have been proposed as alternatives to bromine, as known from U.S. Pat. No. 3,361,803, but their use in practical applications is disfavored because they are consumed in oxidation, not only adding costs for replacing the consumed promoter but also diverting oxygen from desired reactions. These sacrificial promoters can also negatively affect product quality in higher temperature oxidations. N-hydroxyphthalamide has been reported in Y. Ishii, *J. Mol. Catal. A.: Chem*, 1997, 117 (1-3, *Proceedings of the 6th International Symposium on the Activation of Dioxygen and Homogeneous Catalytic Oxidation*, 1996), 123, as a bromine-free alternative promoter for cobalt-catalyzed reactions but its utility in manufacture of aromatic carboxylic acids is limited by its low solubility in acetic acid oxidation reaction solvent, and its consumption, and conversion to undesirable by-products during oxidation due to multiple competing decomposition reactions.

German Patent No. 2804158 describes a process for manufacture of terephthalic acid by solvent-free co-oxidation of p-xylene and/or p-tolualdehyde plus methyl p-toluate to dimethyl terephthalate using a bromine-free catalyst composed of cobalt or manganese salts or a combination of manganese with cobalt or with zinc salts at a temperature in the range of 140-240° C. according to the so-called Witten-Hercules process, followed by catalytic hydrogenation of the total reactor effluent from the co-oxidation in the presence of a palladium, platinum, nickel or cobalt catalyst. The process also includes a heat treatment step for transesterification of terephthalate and p-toluate mono- and diesters from either the co-oxidation or hydrogenation step, which is conducted at 180-350° C. after removal of hydrogen and volatiles. Heat treating is conducted under a nitrogen atmosphere, preferably with addition of water and methanol and, for reducing treatment time, optionally in the presence of Mo, W, Ti, Mg, Ca, Sr, Ba, Mn, Fe, Ni, Zn, Y, K, Y, La, Ce, Nd, Sm, Re, In, Sb, Bi, Se, Te, Sn, P or combinations thereof as catalyst. Absence of bromine from the oxidation catalyst and of monocarboxylic acid reaction solvent in the oxidation are said to permit use of less corrosion-resistant metals for construction of equipment for the co-oxidation and lessen solvent burning.

U.S. Pat. No. 3,865,870 describes a process for oxidizing methylated benzenes to carboxylic acids in which streams of water, methylated benzene feedstock and oxygen-containing gas are fed concurrently over a catalyst metal in a reactor pressurized to 300-1200 psi and at temperatures of 170-300° C. The catalyst metal is silver, palladium, ruthenium, platinum, rhodium, iridium or osmium and is supported on alumina, silica, titania, zirconia, silicon carbide or carbon. Para-xylene oxidations with the patent's preferred metals, ruthenium, palladium or silver, resulted in low yields of oxidized para-xylene derivatives, low aromatic carboxylic acid selectivities (e.g., 3-5% with palladium) and often with significant generation of carbon oxides due to burning of para-xylene feedstock according to the patent's examples.

U.S. Pat. No. 6,160,170 of Codignola discloses oxidation of aromatic feed materials to aromatic carboxylic acids with gaseous oxygen in the absence of bromine in a liquid phase reaction mixture including an aqueous organic solvent using a homogeneous catalytic complex characterized generally as consisting of (A) at least one Group VIIIA metal with a valence greater than 2; and/or at least one Group VIIA metal and/or cerium; and (B) and at least one Group IVA metal which is preferably zirconium or hafnium. (Groups VIIIA, VIIA and IVA referred to in the patent correspond, respectively, to Groups VIII, VIIB and IVB of more recent versions of the Periodic Table according to US Patent Application No. 2002/0188155 A1 of Codignola et al.) Catalyst compositions described in the patent consist of cerium acetate and zirconium acetate, and of ruthenium oxide and zirconium acetate. Practical effectiveness of the catalysts for manufacture of aromatic carboxylic acids is limited because water in amounts commonly present in product recovery or other process steps can rapidly convert zirconium (IV) acetate to zirconium (IV) oxide, which, due to its insolubility in water, can be difficult to separate from aromatic carboxylic acid products recovered in solid form, cause plugging of equipment and catalysts in downstream processing and diminish quality of purified aromatic carboxylic acids products. Precipitated zirconium (IV) oxide also represents a loss of catalyst metal. US Patent Application No. 2002/0188155, noting instability of the catalysts according to International Application WO 98/2938, to which U.S. Pat. No. 6,160,170 corresponds, and reduced activity and selectivity due to their degradation, proposes low temperature (90-150°) oxidation using bromine-free catalytic complexes as in the patent preferably containing a Group VIII metal or cerium and zirconium or hafnium and preferably a mixture of cobalt or cerium and zirconium salts, with filtration of the oxidation product and return of mother liquor from filtration to oxidation, all under substantially the same temperature and pressure conditions. In addition to added complexity of the process, catalysts according to this citation show strong activity for oxidation of acetic acid reaction solvent to carbon oxides unless reaction temperatures are maintained below about 120-140°.

U.S. Pat. No. 5,877,330 describes catalysts prepared from polyvanadic acid sols and other metal compounds for use in gas phase hydrocarbon conversions, reporting 99.5% conversion in high temperature gas-phase oxidation of o-xylene with air at 320° C. with 73.6% selectivity to phthalic anhydride using a calcined combination of polyvanadic acid sol and titanium dioxide and 16.1% conversion of toluene with selectivities of 22.9% to benzaldehyde and 30.1% to benzoic acid using a combination prepared from polyvanadic acid sol and boehmite.

Oxidation of selected aromatic substrates to alcohols and their esterification reactions using catalysts unpromoted with bromine are known from the following patents and publications but oxidation to aromatic carboxylic acids are not described.

Combinations of palladium and antimony are reported useful for production of benzyl mono- and bis-acetates by oxidation of toluene with oxygen gas in an acetic acid solvent to benzyl alcohol and esterification thereof by reaction with the acetic acid according to JP 10265437 A2, and by esterification of mono- or bis-hydroxy products resulting from oxidation of para-xylene in acetic acid according to JP 2004137234 A2. Oxidations did not progress beyond the benzylic alcohols in either case. U.S. Pat. Nos. 5,183,931 and 5,280,001 state generally that alkyl aromatics having a benzylic hydrogen can be oxidized to corresponding oxidized products selected from acids, aldehydes, alcohols and esters by contact in the presence of an oxygen containing fluid in a reaction medium with a catalyst composed of a palladium salt, a lithium, sodium, potassium, magnesium or calcium persulfate, an alkali or alkaline earth metal salt and a tin salt. As demonstrated in the patents' examples, all oxidations were conducted in alkaline reaction media of acetic acid with added potassium acetate and the only reactions exemplified are conversions of p-t-butyl toluene to p-t-butyl benzyl acetate. As in the Japanese publications, oxidations did not proceed beyond formation of the benzylic alcohol, which underwent esterification with acetic acid from the reaction medium.

Tanielyan, S. K. and Augustine, R. L., "Acetoxylation of Toluene Catalyzed by Supported Pd—Sn Catalyst", *J. Mol. Cat.* 1994, 87, 311, reports oxygen uptake in stages corresponding to color changes and residue formation during reaction of toluene with oxygen in acetic acid solvent in the presence of palladium(II) acetate, tin(II) acetate and potassium acetate and proposes a reaction mechanism in which an homogeneous Pd/Sn complex forms and Sn(II) is oxidized to Sn(IV) by oxygen in a first stage, the Pd/Sn(II) complex absorbs oxygen and generates Pd/Sn(III) or Pd/Sn(IV) intermediates which undergo oxidation and reduction reactions to generate Pd(0)/Sn(IV) in a second stage, and the resulting Pd(0)/Sn(IV) catalyzes acetoxylation of the benzylic carbon atom in the third stage.

Other catalytic oxidations of substituted aromatic compounds using catalysts containing or prepared from palladium components and particular other metal components or combinations are reported in U.S. Pat. No. 6,245,936, U.S. Pat. No. 4,804,777 U.S. Pat. No. 6,476,258 and US 2004/0158068. The oxidations according to those patents are conducted in alkaline reaction media and/or for preparation of aryloxyacetic acids from aryloxyethanol starting materials by oxidation of the alcohol of the ring-bonded oxyethanol group but without oxidation of the carbon atoms of ring-bonded carbon-containing substituent groups that may be present in the starting materials.

Antimony (III) is known as a polycondensation catalyst for the manufacture of polyethylene terephthalate from terephthalic acid and glycols. It is considered to have sufficient Lewis acidity to catalyze the polycondensation and not to undergo oxidation, although Leuz, A-K.; Johnson, C. A., *Geochemica et Cosmochimica Acta* 2000, 69(5), 1165, reports that oxidation of trivalent antimony to pentavalent antimony can occur in the presence of oxygen at a pH greater than 9.8 but not at a pH range of 3.6-9.8, or in the presence of hydrogen peroxide at a pH range of 8.1 to 11.7 but not at pH below 8.1.

SUMMARY OF THE INVENTION

This invention provides a process and catalyst composition for conversion of feed materials comprising aromatic hydrocarbons having oxidizable substituent groups to an oxidized aromatic product and with selectivity to aromatic carboxylic acids. Unlike conventional commercial catalysts and processes for making aromatic carboxylic acids such as terephthalic and isophthalic acids, the invented process and catalyst are effective in the substantial or complete absence of bromine sources. While the process and catalyst are tolerant of bromine in some amounts, the presence of bromine in proportions commonly used in conventional commercial processes adversely affects the invented process and catalysts, either reducing conversion to oxidized product or shifting selectivity away from aromatic carboxylic acid products toward aromatic species with less fully oxidized substituent groups. Surprisingly, aromatic carboxylic acid yields according to the invention exceed those achieved with known bromine-free catalyst systems and oxidations proceed beyond the benzylic alcohols and without esterification thereof. In some embodiments, the invention also provides surprising process benefits, including good yields and selectivities when using water as a liquid medium for the reaction and insubstantial generation of carbon oxide by-products due to burning of aromatic feedstock and monocarboxylic acid reaction solvents, such as acetic acid, when used. In some embodiments, water generated as a by-product in the invented process can serve as a liquid reaction medium for the process, with desirable conversion and selectivities, but insubstantial carbon oxide by-product formation even without addition of water or reaction solvents to the process.

In one embodiment, the invention provides a catalytic composition having activity for conversion of aromatic hydrocarbons substituted with oxidizable substituent groups in contact with oxygen in a liquid reaction mixture free of reactive bromine to oxidized aromatic product comprising an aromatic carboxylic acid. The catalytic composition comprises palladium, an element of Group 15 of the Periodic Table of the Elements selected from antimony, bismuth and combinations thereof, and at least one metal or metalloid of Group 4, 5, 6 or 14 of the Periodic Table of the Elements. Except as otherwise stated, Groups of the Periodic Table of the Elements referred to herein correspond to "New Notation" designations according to the Periodic Table of the Elements as found, for example, in the Handbook of Chemistry and Physics, 78th Edition, CRC Press, 1997. The terms "Group" and "Groups" in reference to elements, metals and metalloids will be understood to refer to Groups of such a Periodic Table of the Elements.

As used herein, "conversion of substituted aromatic compounds" refers to conversion of the compounds to oxidized aromatic derivatives and accordingly, for purposes hereof, expressions such as "oxidized aromatic derivatives" and "oxidized aromatic product" do not include carbon monoxide or carbon dioxide generated due to burning of aromatic starting materials or oxidation products. "Selectivity to aromatic carboxylic acid" refers to the weight of oxidized aromatic derivative or derivatives substituted with at least one carboxylic acid group expressed as a percentage of the total weight of oxidized aromatic derivatives.

In another aspect, the invention provides a process for making a catalytic composition. In one embodiment, this aspect of the invention provides a process for making a catalytic composition which has activity for conversion of substituted aromatic hydrocarbons having oxidizable substituent groups in contact with oxygen in a liquid reaction mixture free of reactive bromine to an oxidized aromatic product comprising aromatic carboxylic acid. The process for making such a catalyst composition comprises combining in an aqueous $C_{1-8}$ monocarboxylic acid solvent and in the substantial absence of reactive bromine components that are soluble in the solvent and comprise palladium salt, at least one Group 15 element selected from antimony, bismuth and a combination thereof and at least one Group 4, 5, 6 or 14 metal or metalloid. Catalyst solutions prepared as described above are suitable for use in oxidation of substituted aromatic hydrocarbons according to the process of this invention. The solutions alternatively can be used for preparation of unsupported or supported solid catalyst compositions Another aspect of the invention is a process for conversion of feed materials comprising substituted aromatic compounds to oxidized aromatic products with selectivity to aromatic carboxylic acids. According to embodiments of this aspect of the invention, a process for conversion of an aromatic feedstock comprising a substituted aromatic hydrocarbon having one or more oxidizable substituent groups to an aromatic oxidation product comprising aromatic carboxylic acid comprises contacting the aromatic feedstock with oxygen in a liquid reaction mixture in the presence of a catalyst composition comprising palladium, a Group 15 element selected from antimony, bismuth or a combination thereof and at least one Group 4, 5, 6 or 14 element. Preferably, the catalyst composition is free of bromine and is contacted with the aromatic feedstock in the absence of bromine.

In other embodiments, a process for manufacture of aromatic carboxylic acid comprises contacting a feed material comprising at least one dialkylarene, partially oxidized dialkylarene derivative or combination thereof, with oxygen in a liquid reaction mixture comprising water or water and a monocarboxylic acid solvent at temperature and pressure effective to maintain a liquid phase reaction mixture in the presence of a catalyst according to the invention.

The invention also provides aromatic carboxylic acid compositions, and especially terephthalic acid, isophthalic acid and naphthalene dicarboxylic acid compositions prepared according to processes of the invention or using catalyst compositions according to the invention. A terephthalic acid composition according to a preferred embodiment of the invention comprises terephthalic acid and, by weight thereof, about 0.1 to about 500 ppmw of palladium, calculated as the element, about 0.1 to about 500 ppmw antimony, bismuth or a combination thereof, calculated as elements, and about 0.1 to about 500 ppmw of a Group 4, 5, 6 or 14 metal or metalloid, calculated as elements, or combinations thereof. In another embodiment, a terephthalic acid composition suitable for direct conversion by reaction with at least one glycol to polyester suitable for manufacture of fiber comprises terephthalic acid and, by weight of the terephthalic acid, about 0.01 to about 100 ppmw palladium, calculated as the element, about 0.01 to about 100 ppmw antimony, bismuth or combination thereof, calculated as elements, and about 0.01 to about 100 ppmw Group 4, 5, 6 or 14 metal or metalloid, calculated as elements, or a combination thereof.

DETAILED DESCRIPTION OF THE INVENTION

Catalyst compositions according to aspects and embodiments of the invention comprise palladium, a Group 15 element selected from antimony, bismuth or a combination of antimony and bismuth, and at least one Group 4, 5, 6 or 14 metal or metalloid. The expression "metal or metalloid" is used herein to refer collectively to metallic elements as well as semi-metallic and other elements not considered metals in a strict sense but having metal-like properties. In referring to metals and metalloids and components of the catalyst composition, it will be understood that the terms are used in a broad sense to include the metals and metalloids as such as well as their compounds, complexes, alloys and combinations in other forms. Among the Group 4, 5, 6, 14 and 15 elements included in catalyst compositions according to aspects of the invention, arsenic, antimony, and bismuth of Group 15 and tellurium and polonium of Group 16 are or may be considered metalloids. Other elements that may be considered metalloids include boron, aluminum, silicon and germanium. Significance of distinctions between metals and metalloids is not readily apparent for purposes of the invention.

In addition to palladium, the invented catalyst compositions include a Group 15 element which is antimony, bismuth or a combination thereof. Catalyst compositions comprising antimony are preferred due to their greater conversions and selectivities than compositions in which the Group 15 component is only bismuth.

The catalyst compositions also include at least one Group 4, 5, 6, or 14 metal or metalloid. Specific examples of those metals and metalloids include Group 4 metals such as titanium, zirconium and hafnium, Group 5 metals such as vanadium, niobium and tantalum, Group 6 metals such as molybdenum, chromium and tungsten and Group 14 metals or metalloids such as germanium, tin and lead. Preferred Group 4, 5, 6 and 14 metals and metalloids include titanium, vanadium, chromium, niobium, molybdenum, tin and combinations thereof. Preferred metal and metalloid components and combinations vary somewhat depending on other components of the invented compositions. Combinations of antimony or bismuth and one or more of titanium, vanadium, molybdenum, chromium, niobium and tin often provide desirable results in oxidations according to the invention. According to embodiments of the invention, catalyst compositions containing palladium, antimony and one or more of tin, vanadium and molybdenum provide surprising conversions of substituted aromatic hydrocarbon substrates to oxidized products and selectivities to aromatic carboxylic acids. In another embodiment, combinations of bismuth and niobium provide beneficial results.

The specific form and chemical identity of the catalytically active specie or species of the invented catalytic compositions is not known. Accordingly, the description herein of the invented catalytic compositions in terms of their constituent elements, metals, metalloids or components is intended to include the form or forms and composition or compositions in which the components are catalytically active, whether that be as mixtures or combinations of discrete metals or metalloids or compounds thereof or as complexes, reaction products or other combinations thereof. Water- and organic acid-soluble and insoluble forms of the catalytic compositions have been observed to exhibit activity for oxidation of oxidizable substituents of substituted aromatic compounds and selectivity to aromatic carboxylic acid oxidation products. Accordingly, in oxidation processes conducted in the presence of water, aqueous monocarboxylic acid reaction solvents and other liquid reaction media, the invention includes use of homogeneous and heterogeneous forms of catalyst composition, as well as hybrid forms in which the catalyst composition is made up of components in both homogeneous and heterogeneous forms, as where one or more heterogeneous components comprises an unsupported or supported metal, metalloid or combination thereof that is insoluble in the liquid reaction mixture and one or more components soluble in the liquid reaction medium is present as a homogeneous component.

In some embodiments, a form of the invented catalytic compositions is a solution comprising palladium, one or both of antimony and bismuth, and Group 4, 5, 6 or 14 metal or metalloid components or combinations thereof in a suitable solvent such as water or an organic acid or aqueous organic acid. Such a solution is suitably prepared by combining soluble metal or metal and metalloid compounds. Preferred organic solvents are $C_{1-8}$ monocarboxylic acids and aqueous solutions thereof and especially acetic acid or aqueous acetic acid. Water is also a preferred solvent for preparation of catalyst composition or component solutions and especially for preparing solutions for use in liquid phase oxidations according to the invention in which a liquid reaction medium for the oxidation reaction mixture is wholly or largely water. Suitable metal or metalloid compounds are at least partially soluble in the water or acidic preparation solvent or form at least partially soluble species on combination with salts or compounds of the other metals or metalloids used in preparing the compositions. Carboxylate salts of the metals and metalloids, such as acrylates, acetates, propionates, butyrates, hexanoates, cyclohexanoates, oxalates, and benzoates, and preferably those with 2 to about 10 carbon atoms, are generally preferred owing to their solubility in common organic solvents and availability. For a given metal or metalloid, other suitable compounds can include oxides, hydroxides, carbonates, chlorides, nitrates, sulfates, sulfites, methanesulfonates, trifluoromethanesulfonates, tetrafluoroborates, oxides, acetylacetonates, methoxides, ethoxides, propoxides, butoxides, and other alkoxides, hydrides, phosphates and combinations thereof. Bromine-free salts and compounds of the metals and metalloids used for preparing the catalytic compositions are preferred because presence of reactive bromine at high enough concentrations in oxidation reaction mixtures using the invented catalyst compositions has been seen to correlate with decreases in activity and selectivity of the catalyst compositions and undesired precipitation of soluble metal or metalloid components from the reaction mixtures. Preferred metal and metalloid salts also are free of halogens other than bromine although such other halogens may be present provided they do not cause undesirable corrosion in use of the catalytic compositions or adversely affect activity or selectivity of the compositions.

Another preferred form of the invented catalytic compositions comprises a water and/or monocarboxylic acid-insoluble composition formed from palladium, antimony, bismuth or a combination thereof and one or more Group 4, 5, 6 or 14 metal or metalloid compounds or combinations thereof. Such insoluble compositions are conveniently prepared by contacting solutions of individual or combined metal and metalloid compositions such as described in the previous paragraph, with the metal and metal or metalloid compositions, contacting conditions or additional preparative steps selected to yield a wholly or partially solid product. In one embodiment, a solid catalyst composition is conveniently prepared by contacting a solution of metal and metal or metalloid compounds with air or another oxygen source at above-ambient temperatures such as about 80° C. or greater and preferably at about 90° C. to about 150° C. In some embodiments, the insoluble reaction product is a catalytically active composition while in other embodiments, the insoluble portion exhibits activity in combination with a soluble portion remaining after reaction to form the insoluble product. By way of example, combining acetic acid solutions of palladium(II), antimony(III) and tin(II) acetates under an inert atmosphere in amounts providing approximately equimolar palladium, antimony and tin tends to yield a solid precipitate which is active for oxidation of substituted aromatic compounds. When an acetic acid solution of molybdenum(II) acetate dimer providing approximately equimolar molybdenum is also included in the solution, solid precipitate comprising substantially all of the palladium, antimony and tin but only a portion of the molybdenum forms with another portion of the molybdenum remaining in solution, with both the solid portion and its combination with the insoluble portion showing activity. When the solutions are contacted in the presence of oxygen, solid comprising essentially all of the palladium, antimony, tin and molybdenum is obtained and is active.

Another suitable form of the invented catalyst compositions comprises at least one of palladium, antimony or bismuth and or Group 4, 5, 6 or 14 metal or metalloid components carried on a solid support material in the form of a supported catalyst composition or component. Preferred supported catalyst compositions comprise palladium, antimony and one or more of tin, molybdenum and vanadium carried on a support material.

Metal and metalloid components used to prepare catalyst solutions or insoluble catalyst compositions or components can be in any valence state that provides a composition having activity and selectivity under conditions of use for oxidation of substituted aromatic compounds in which substituent groups comprise an oxidizable alpha carbon to oxidized product comprising aromatic carboxylic acid derivatives of the substituted aromatic compound.

Specific examples of suitable palladium compounds for preparing catalytic compositions include Pd(II) acetate, Pd(II) acetylacetonate, Pd(II) propionate, Pd(II) nitrate, Pd(II) cyanide, Pd(II) hydroxide, Pd(II) oxide, Pd(II) sulfate and Pd(II) sulfide. Halide salts, such as chlorides or iodides, can be use in preparation of solid or supported catalyst compositions or components in which halogen derived from the starting salts is not, or is only negligibly, present in the final supported composition. For preparation of catalyst compositions or palladium components thereof in the form of solutions in water or aqueous organic acids, however, use of halide salts and especially bromides, is preferably avoided. For preparation of supported catalyst compositions in which palladium, either alone or with other metals or metalloids of the compositions, is carried on a support, palladium supported on a suitable support material such as described below and palladium(0) alloys also are useful.

Examples of useful Group 15 metal or metalloid compounds are compounds of antimony or bismuth such as Sb(III) acetate, Sb(III) butoxide, Sb(III) ethoxide, Sb(III) isopropoxide, Sb(III) methoxide, Sb(III) oxide, Sb(IV) oxide, Sb(V) oxide, Sb(III) propoxide, Sb(III) sulfide, Sb(V) sulfide, antimony tin oxide; bismuth salts such as Bi(III) acetate, Bi(III) carbonate, Bi(III) chloride, Bi(III) citrate, Bi(III) fluoride, Bi(V) fluoride, Bi(III) iodide, Bi(III) molybdate, Bi neodecanoate, Bi(III) nitrate, Bi(III) oxide, Bi(III) oxychloride, Bi(III) perchlorate, Bi(III) phosphate, Bi(III) salicylate, Bi(III) sulfide, Bi(III) titanate and Bi(III) triflate.

Examples of Group 4 metal compounds that are suitable for catalyst composition preparation include Ti(IV) butoxide, Ti(IV) carbide, Ti(IV) carbonitride, Ti(IV) diisopropoxide bis(acetylacetonate), Ti(IV) ethoxide, Ti(II) hydride, Ti(IV) isopropoxide, Ti(IV) methoxide, Ti(IV) nitrate, Ti(IV) nitride, Ti(IV) oxide, Ti(II) oxide acetylacetonate, Ti(IV) oxysulfate, Ti(IV) propoxide, Ti(III) sulfate and Ti(IV) sulfide; zirconium compounds such as Zr nitride, Zr(IV) oxide, Zr(IV) sulfate, Zr(IV) nitrate, Zr(IV) propoxide, Zr(IV) trifluoroacetylacetonate, Zr(IV) chloride, Zr(IV) perchlorate, Zr(IV) iodide, Zr(IV) hydroxide, Zr(IV) fluoride, Zr(IV) ethoxide, Zr(II) hydride, Zr(IV) hydrogenphosphase; and hafnium compounds exemplified by Hf(IV) t-butoxide, Hf(IV) carbide, and Hf(IV) sulfate.

Examples of useful Group 5 metal compounds include vanadium compounds such as V(III) acetylacetonate, V(IV) carbide, V(IV) oxide sulfate, V(V) oxytriethoxide, V(V) oxytriisopropoxide, V(V) oxytripropoxide, vanadium oxide acetylacetonate, vanadium oxide 2,3-naphthalocyanine; and niobium compounds such as Nb(IV) carbide, Nb (V) chloride, Nb(IV) chloride, Nb(III) chloride, Nb(V) ethoxide, Nb(V) fluoride, Nb(V) iodide and Nb nitride.

Examples of useful Group 6 compounds include molybdenum compounds such as Mo(II) acetate, Mo(II) carbide, Mo(0) hexacarbonyl, Mo(VI) oxide, Mo(IV) sulfide, molybdic acid and various molybdates ($MoO_4^-$); chromium salts including Cr(III) acetate, Cr(III) acetylacetonate, Cr(III) carbide, Cr hexacarbonyl, Cr(III) nitrate, Cr(III) nitride, Cr(III) oxide, Cr(VI) oxide, Cr(III) phosphate, Cr(III) sulfate, and various chromates ($CrO_4^-$) and dichromates ($Cr_2O_7^-$)

Examples of useful Group 14 metal or metalloid compounds include Ge acetate, Ge(IV) chloride, Ge(IV) ethoxide, Ge(IV) fluoride, Ge(IV) iodide, Ge(IV) isopropoxide, Ge(IV) methoxide, Ge(III) nitride, Ge(IV) oxide and Ge(II) sulfide; tin compounds such as Sb(II) acetate, Sb(IV) acetate, Sb(II) oleate, Sb(IV) t-butoxide, Sb(II) 2-ethylhexanoate, Sb(II) hydride, Sb(II) iodide, Sb(II) methanesulfonate, Sb(II) 2,3-naphthalocyanine, Sb(II) oxalate, Sb(II) oxide, Sb(II) phthalocyanine, Sb(II) pyrophosphate, Sb(II) sulfate and Sb(II) sulfide; and lead compounds such as Pb(II) acetate, Pb(IV) acetate, Pb(II) acetylacetonate, Pb(II) carbonate, Pb(II) chloride, Pb(II) fluoride, Pb(II) iodate, Pb(II) iodide, Pb(II) methanesulfonate, Pb(II) molybdate, Pb(II) niobate, Pb(II) nitrate, Pb(II) oxide, Pb(IV) oxide, Pb(II) perchlorate, Pb(II) phthalocyanine, Pb(II) salicylate, Pb(II) sulfate, Pb(II) sulfide, Pb(II) tetrafluoroborate, Pb(II) thiocyanate, Pb(II) titanate, Pb(II) trifluoroacetate, Pb(II) tungstate and Pb(II) zirconate.

Halides of the metals and metalloids included above are suitable used in preparing supported or other solid catalyst compositions and components from which halogen from starting materials is absent or present in only traces, but not in preparing soluble forms of the invented catalyst or their components. As with palladium, supported and other insoluble forms of the Group 4, 5, 6 and 14 metals and metalloids, including their alloys also are useful in preparing solid and supported catalysts and components.

Additional metals and metalloids, e.g., aluminum, gold, calcium, cadmium, cerium, copper, iron, gallium, indium, iridium, potassium, lithium, sodium, rhodium, ruthenium, selenium, zinc and combinations thereof may be included in the compositions although their effects can vary depending on other components of the compositions and amounts in which they are used. Compounds of other metals and metalloids that may be used for preparation of catalyst compositions include acetates, oxalates, benzoates and other carboxylates, hydroxides, nitrates, sulfates, sulfites, oxides, hydrides, carbonates, phosphates, perchlorates, methanesulfonates, trifluoromethanesulfonates, tetrafluoroborates, acetylacetonates, methoxides, ethoxides, propoxides, butoxides and other alkoxides, as well as solid and supported forms and alloys thereof. Selection of such additional metals or metalloids and combinations varies with choices and combinations of platinum, antimony or bismuth and Group 4, 5, 6 or 14 metals or metalloids. In a specific embodiment of the invention, catalyst compositions containing palladium and bismuth are enhanced by inclusion of gold, which can conveniently be used in catalyst or component preparations in the form of gold(I) sulfide gold(I) cyanide, gold(II) hydroxide, gold(II) oxide, and gold(II) sulfide; chlorides and iodides such as gold(I) chloride or iodide and gold(II) chloride may also used but are less preferred for preparing soluble compositions and components due to potential corrosion from chlorides and iodides.

Organic acid solutions of the palladium, antimony, bismuth and Group 4, 5, 6 and 14 metals or metalloids of the catalyst compositions are preferred forms of the invented compositions not only due to ease of preparation and availability of common metal and metalloid compounds useful for their preparation but also because they are in a form compatible with use of the catalytic compositions in oxidation of substituted aromatic feed materials in liquid phase reaction systems. It may also be desirable in some embodiments that the catalytic composition be formed by separate or sequential addition of metal and/or metalloid compounds or components or combinations thereof such that a final catalytic composition is formed on addition to the liquid reaction mixture used for oxidation of substituted aromatic feed materials. While a preferred form of the compositions comprises a solution of metal and/or metalloid components in a carboxylic acid or aqueous carboxylic acid solvent, it also is to be understood that the invention includes other forms of the catalytic composition or its constituent metals, metalloids or combinations thereof.

In another preferred embodiment of the invention, catalytic compositions or components thereof are formulated with support materials. The catalytic composition or components can be deposited or otherwise combined with the support material by any suitable technique, such as by contacting a support material, for example in the form of pellets, granules, extrudate or other particulate or solid form suited to process use, with a solution of catalyst metal compounds in water or another solvent that is inert to the support and easily removed, after which the solvent is removed, such as by drying at ambient or elevated temperature. For such preparations, a single solution of all catalyst metal or metalloid salts or compounds can be employed as can concurrent or sequential impregnations with solutions of individual catalyst metals or metalloids or combinations. Support materials pre-impregnated with one or more metals or metalloids, for example supported palladium components, can be contacted with a solution or solutions of other catalyst metal or metalloid. So-called "incipient wetness techniques," in which a support is contacted with a solution of the catalyst metal or metalloid compound in an amount that just wets the support and then the resulting wetted support is dried, are known and well suited to manufacture of the catalysts. In another suitable technique, sometimes referred to as the "excess solution method," the support is contacted with a greater volume of one or more impregnation solutions than required to wet the support, after which solvent is removed by drying, for example by evaporation under ambient conditions or with moderate heating.

Excess solution techniques are sometimes preferred over incipient wetness methods when using low surface area supports. Other techniques, such as spraying a solution of catalyst metal compound or compounds onto a support material also are suitable. Post-treatments, such as heating and high temperature calcinations in the presence of air or nitrogen, and reduction with hydrogen also may be yield catalyst compositions or components with advantages or characteristics of interest.

For use in the invented process, any carrier for the catalyst composition or components thereof that is stable in the environment and under conditions of process use is suitable. Preferred support materials are solids that are stable in the sense of maintaining physical integrity and metal or metal and metalloid loadings suitable to process operation over prolonged exposures to process conditions and use. Substantial insolubility of the support and resistance to significant loss of catalyst metal or metalloid loadings in water or aqueous acetic acid solutions at temperatures of at least about 100° C. for a period on the order of several days, for example at least 7 days, are indicative of suitable support materials. Preferred supports for use in the invented process include carbons and non-zeolitic metal oxides such as alpha alumina, silicas and titania, including rutile and anatase forms thereof and mixed forms in which both anatase and rutile phases are present. Non-zeolitic supports are preferred because zeolites tend to lack adequate stability for use in oxidations according to the invented process. Other supports which may be suitable include high strength, acid stable silicon carbides, zirconia, gamma alumina and zinc oxide. Common examples of suitable commercially available carbon supports tend to have BET surface areas ranging from about one or even a fractional square meter per gram up to about 1500 $m^2/g$. Metal oxide surface areas tend to run from about 1 $m^2/g$ in the case of rutile titanias up to about 500 $m^2/g$ for silicas. Support materials can be used in any suitable form, examples of which include powders, particulates, pellets, extrudate, tablets, granules, spheres and microspheres. Catalyst metal loadings of supported compositions are not critical though loadings in the range of about 0.1, and preferably 0.5 to about 20 and preferably 15 percent by weight of the supported composition are preferred for high catalyst performance and activity.

Proportions of the palladium, antimony, bismuth, Group 4, 5, 6, and 14 metal or metalloid components of the invented catalytic compositions can vary widely. Preferably, palladium and one or both of antimony and bismuth are present in amounts such that the atom ratio of palladium, to antimony, bismuth or their combination is about 1:1000 to about 1000:1, and more preferably about 1:100 to about 100:1. Proportions of palladium and Group 4, 5, 6 or 14 metal or metalloid also are preferably present in atom ratios of about 1:1000 to about 1000:1 and more preferably about 1:100 to about 100:1. Proportions of metal and metalloid elements in various combinations can be determined and optimized for particular combinations and usages by persons skilled in catalytic oxidations for manufacture of benzene and naphthalene dicarboxylic acids guided by the description and examples appearing herein.

A preferred catalytic composition according to embodiments of the invention comprises a palladium component, at least one antimony or bismuth component and tin, titanium, molybdenum, vanadium, chromium, niobium or a combination thereof. Especially preferred compositions comprise a palladium component, an antimony component and at least one component of tin, titanium, vanadium or molybdenum. Another particularly preferred composition comprises a palladium component, a bismuth component, and at least one tin, titanium, niobium, molybdenum or vanadium component. Addition of other metals such as gold, gallium, calcium and zinc to such compositions can also be beneficial.

Such compositions can exhibit desirable activities for oxidation of substituted aromatic substrates according to the invention with good selectivity to aromatic carboxylic acid derivatives and, in some embodiments, relatively low burning of aromatic substrates and organic acid reaction solvents to carbon oxides. As described above, atom ratios of the palladium and other metal or metalloid in such compositions can vary widely and can be optimized or tailored to applications by routine experimentation guided by the disclosure herein. Palladium and other metal or metalloid component or components are preferably present in amounts such that the atom ratio of palladium to each other metal or metalloid is about 1:100 to about 100:1. More preferably, in compositions comprising palladium and antimony or bismuth, the atom ratio of antimony and/or bismuth to each such other metal or metalloid also is about 1:10 to about 10:1. Preferably, the compositions are free or at least substantially free of reactive bromine. In some embodiments, compositions according to invention in which the atom ratio of palladium to one or more of antimony or bismuth is about 1:1 and more preferably about 1.5:1 to about 10:1 and more preferably about 5:1, and in which the atom ratio of palladium to one or more additional metals or metalloids such as molybdenum, titanium or vanadium or tin is about 0.3:1, and preferably about 1:1 to about 5:1 and more preferably about 3:1, are highly effective for oxidations with high conversions and selectivities. A specific example of such a catalyst that is particularly effective composition for oxidation of disubstituted aromatic compounds with high conversion and selectivity to corresponding aromatic dicarboxylic acids includes a palladium component, an antimony component, and a vanadium or molybdenum component or a combination thereof or of either with another metal or metalloid component such as chromium, titanium or tin, in amounts such that the atom ratio of palladium to antimony or bismuth (or a combination thereof) to molybdenum, vanadium, tin or combination thereof with each other or such other metals or metalloids is about 1:1:0.5.

The mechanism or mechanisms by which the invented compositions catalyze reaction of oxidizable substituent-bearing aromatic compounds with oxygen to oxidized products with selectivity to aromatic carboxylic acids is not understood. The compositions exhibit activity for oxidation of alkyl-substituted aromatics as well as partially oxidized derivatives thereof, such as toluic acids, hydroxymethyl benzoic acids, aromatic aldehydes and carboxybenzaldehydes, to more completely oxidized carboxylic acid derivatives. As seen from the Examples herein, certain of the individual metals and metalloids of the invented compositions exhibit some activity for conversion of para-xylene to oxidized aromatic derivatives thereof; however, conversions are accompanied by highly varying selectivities to oxidized derivatives of the para-xylene and often by comparable or even greater burning of the para-xylene to carbon oxides. However, compositions in which palladium, antimony or bismuth, and one or more Group 4, 5, 6 or 14 or 15 metal or metalloid are present showed increased and often unexpected conversions to oxidized aromatic derivatives, selectivities, reduced carbon oxide generation or combinations of those improvements and, in some cases, potential for further improvement by addition of combinations of Group 4, 5, 6 or 14 metals or metalloids.

Activity and selectivity of the invented compositions have been demonstrated in liquid reaction media, including essentially neutral systems such as water as well as mildly and strongly acidic media. The invented compositions show surprising differences in sensitivity to water as compared to known, bromine-promoted catalysts for oxidation of alkyl aromatics. Known bromine-promoted catalysts used in commercial manufacture of terephthalic acid by oxidation of para-xylene or of isophthalic acid by oxidation of meta-xylene tend to fall off in conversion activity in aqueous acetic acid reaction media with increases in water content of as little as 1 wt %. In contrast, with catalytic compositions according to embodiments of the invention, oxidations continued to progress actively even as water concentrations in liquid reaction media increased to almost 50%. In para-xylene oxidations with the invented compositions, selectivity to fully oxidized terephthalic acid product was virtually unchanged at water levels ranging from about 5 to about 40 wt %, and selectivities to partially oxidized intermediates capable of further oxidation to terephthalic acid tended to decrease in minor amounts, which is an indication of increased catalytic activity. Even with 100 wt % water as liquid reaction medium, oxidation ranged from modest to vigorous while selectivity to aromatic carboxylic acids was generally greater than 50% and as high as 80% or more.

Compositions according to embodiments of the invention exhibit activity and selectivity for converting substituted aromatic hydrocarbons having oxidizable substituents to carboxylic acid derivatives, with relatively low levels of burning of the substrate compounds or of organic acids used as reaction solvents. Generation of carbon oxides tends to increase with increasing temperature, other things being equal, and conversion to carbon dioxide appears to be favored over carbon monoxide.

The compositions are active for oxidation of substituted aromatic substrates and show selectivity to aromatic carboxylic acids in the absence of reactive bromine. In oxidation trials conducted with added aqueous hydrogen bromide as a source of reactive bromine, neither conversions to oxidized aromatic derivatives nor selectivities to carboxylic acid derivatives were improved. The invented catalyst compositions appear to be tolerant of small amounts of reactive bromine in oxidation of substituted aromatic hydrocarbon substrates, although amounts of less than 5% by weight of total catalyst metal and metalloid have been observed to deactivate the compositions in the sense that selectivity to carboxylic acid derivatives is more favorable to less fully oxidized products such as aldehydes and, in conversions of di-substituted aromatics, to derivatives with a single carboxylic acid group and one or more unconverted or only partially oxidized group such as an hydroxymethyl or aldehyde group. With still larger amounts of bromine, at least some of the compositions according to the invention show loss of conversion, to the point that little or no oxidized product is obtained. Preferably reactive bromine is present at levels less than about 2 wt % based on catalyst metal and metalloid weight.

The invented compositions also appear to deactivate with increasing levels of methyl ethyl ketone, which is a known sacrificial, organic promoter for cobalt-based catalysts used for oxidation of alkyl aromatics. At low levels, activity and selectivity appear relatively unaffected but at greater levels, conversion drops and selectivity shifts away from aromatic carboxylic acids toward less fully oxidized derivatives.

Although catalytic mechanisms and reaction pathways of the invented catalytic compositions are not understood, the compositions are effective for oxidation of substituted aromatic substrates, exhibiting activity for substantial conversion of substituent groups to more fully oxidized derivatives substituted with aldehyde groups, carboxylic acid groups or combinations thereof with selectivity to carboxylic acid groups, and without need for use of bromine to promote the oxidation. Activity and selectivity of the compositions in the absence of reactive bromine afford a number of benefits and opportunities for advantage over conventional processes for oxidizing aromatic substrates using bromine-promoted catalysts, as well as alternative proposals that rely on catalysts with low activities and selectivities, alkaline reaction media or catalysts prone to conversion to insoluble precipitates that can cause plugging in other process steps. In the manufacture of aromatic carboxylic acids from aromatic feed materials, and particularly alkyl aromatic hydrocarbons such as toluene, xylenes and methyl naphthalenes, the invention can provide opportunities for process simplification and costs savings by allowing bromine to be eliminated from oxidation process and catalyst systems. Such opportunities include potential not only for eliminating or reducing requirements for treatment of process effluents, such as by thermal or catalytic oxidation and scrubbing, to eliminate unwanted brominated by-products of the process, but also for downgrading metallurgy of reaction vessels, agitators and associated reaction off-gas treatment equipment, such as condensers, distillation columns and the like, from expensive titanium metal and nickel alloy steel solid and clad constructions commonly required for conventional bromine-promoted catalytic oxidations to less corrosion resistant constructions such as stainless or mild steels or with reduced cladding. Furthermore, high temperature oxidations, for example at temperatures of about 170° C. and greater, can be conducted without substantial burning of aromatic substrates or carboxylic acid solvents to carbon oxides. Oxidations in water or dilute aqueous organic acid liquid reaction media or solvents also provide opportunities for reduced organic solvent usage, reduced corrosivity of reaction mixtures, process streams, effluents and off-gases and potential for process simplification and additional downgrading of materials of construction for process equipment.

Briefly, the invented process provides for conversion of an aromatic feedstock comprising a substituted aromatic hydrocarbon having oxidizable substituents to oxidized aromatic product comprising at least one aromatic carboxylic acid derivative of the substituted aromatic compound by contacting the aromatic feedstock with oxygen in a liquid reaction mixture in the presence of a catalytic composition according to the invention. Preferred substituted aromatic hydrocarbons are those in which at least one substituent group includes an oxidizable alpha carbon atom. In this context, an "alpha carbon atom" refers to a carbon atom linked directly to an aromatic ring and an "oxidizable alpha carbon atom" is an alpha carbon atom having at least one hydrogen bonded directly to it. Oxidation of substituted aromatic feed materials with oxidizable alpha carbon atom-containing substituents is selective to aromatic carboxylic acid derivatives in which at least one substituent group is a carboxylic acid group having an alpha carbon atom but the oxidation product can also include derivatives with less fully oxidized substituents or in which one but not all of the substituent groups of the starting material is oxidized to a carboxylic acid group while other groups are less fully oxidized or remain unconverted. Other things being equal, conversions and selectivities with the invented catalytic compositions exceed those using individual metals or metalloids of the compositions. Conversion to oxidized aromatic derivatives of aromatic starting materials preferably is at least about 25 mole % and, in some embodiments of the invention, approaches 100 mole %. Selectivity to aromatic carboxylic acid derivatives, taking into account all carboxylic acid-substituted oxidation products of the aromatic feed material, is preferably at least about 40% and can approach 100%. According to some embodiments of the invention, conversions of at least about 80 mole % with at least 80%, and more preferably 90% or greater, selectivity to a single aromatic acid derivative are achieved such that the invention provides processes for manufacture of such derivatives in which recovery techniques and recycle of intermediate oxidation products can be minimized or simplified. Preferred aromatic carboxylic acids for which embodiments of the invented process is suited are those manufactured in a liquid phase reaction system and include mono- and polycarboxylated species having one or more aromatic rings in which at least one, and preferably all, of the carboxylic acid groups comprise a carbon atom linked directly to the aromatic ring, i.e., an alpha carbon atom. Examples of such aromatic acids include terephthalic acid, trimesic acid, trimellitic acid, phthalic acid, isophthalic acid, benzoic acid and naphthalene dicarboxylic acids.

Liquid phase oxidation according to embodiments of the invented process is conducted at elevated temperature and pressure, and preferably under pressure effective to maintain a liquid phase reaction mixture. Oxidation of the aromatic feed material in the liquid phase oxidation step produces oxidized product comprising aromatic carboxylic acid as well as reaction by-products such as partial or intermediate oxidation products of the aromatic feed material. The liquid-phase oxidation and associated process steps, such as product recoveries, separations, purifications and off-gas and liquid effluent treatments, can be conducted as a batch process, a continuous process, or a semi-continuous process.

Suitable aromatic feed materials for the oxidation generally comprise an aromatic hydrocarbon substituted at one or more positions, normally corresponding to the positions of the carboxylic acid groups of the aromatic carboxylic acid being prepared, preferably with at least one group that includes an alpha carbon atom that is oxidizable to a carboxylic acid group. The oxidizable substituent or substituents can be alkyl groups, such as a methyl, ethyl or isopropyl groups, or groups already containing oxygen, such as a hydroxyalkyl, formyl or acyl group. The substituents can be the same or different. The aromatic ring of feedstock compounds can be a benzene nucleus or it can be bi- or polycyclic, such as a naphthalene nucleus. The number of oxidizable substituents on the aromatic portion of the feedstock compound can be equal to the number of sites available on the aromatic ring, but is generally fewer than all such sites and preferably 1 or 2 and most preferably 2. Examples of useful feed compounds, which can be used alone or in combinations, include toluene, ethylbenzene and other alkyl-substituted benzenes, o-xylene, p-xylene, m-xylene, tolualdehydes, toluic acids, alkyl benzyl alcohols, 1-formyl-4-methylbenzene, 1-hydroxymethyl-4-methylbenzene, methylacetophenone, 1,2,4-trimethylbenzene, 1-formyl-2,4-dimethylbenzene, 1,2,4,5-tetramethylbenzene, alkyl-, formyl-, acyl-, and hydroxylmethyl-substituted naphthalenes, such as 2,6-dimethylnaphthalene, 2,6-diethylnaphthalene, 2,7-dimethylnaph-thalene, 2,7-diethylnaphthalene, 2-formyl-6-methylnaphthalene, 2-acyl-6-methylnaphthalene, 2-methyl-6-ethylnaphthalene and partially oxidized derivatives of the foregoing.

For manufacture of aromatic carboxylic acids by oxidation of their correspondingly substituted aromatic hydrocarbon pre-cursors, e.g., manufacture of benzoic acid from mono-substituted benzenes, terephthalic acid from para-disubstituted benzenes, phthalic acid from ortho-disubstituted benzenes, and 2,6- or 2,7-naphthalenedicarboxylic acids from, respectively, 2,6- and 2,7-disubstituted naphthalenes, it is preferred to use relatively pure feed materials, and more preferably, feed materials in which content of the precursor corresponding to the desired acid is at least about 95 wt. %, and more preferably at least 98 wt. % or even higher. Preferred precursors include alkyl aromatic compounds as well as their partially oxidized derivatives. By way of example, in the case of para-xylene, examples of partially oxidized derivatives that also can be converted to more fully oxidized product comprising aromatic carboxylic acid include derivatives such as p-methylacetophenone, p-toluic acid, p-hydroxymethyl benzoic acid, tolualdehyde and 4-carboxybenzaldehyde. A preferred aromatic hydrocarbon feed for use to manufacture terephthalic acid comprises para-xylene. A preferred feed material for making benzoic acid comprises toluene.

Oxidation of aromatic feed materials according to the invented process is conducted in a liquid reaction mixture. Acidic reaction media are preferred. Water can be used as the reaction medium with surprisingly good conversions and selectivities. Water generated as by-product in oxidations of aromatic feed materials according to the invention can serve as liquid medium for the reaction, thereby eliminating or reducing the need for addition of water to the process from external sources or by recycle of water from other process steps and also eliminating use or presence of different liquids and process and equipment complexities that may be needed for their separation and recycle or re-use. In one embodiment, a preferred liquid medium for the reaction mixture comprises water and not more than about 10% $C_1$-$C_8$ monocarboxylic acid. Preferred solvents for aromatic feed materials in the liquid phase reaction comprise low molecular weight monocarboxylic acids and preferably a $C_1$-$C_8$ monocarboxylic acid, for example acetic acid, propionic acid, butyric acid, valeric acid and benzoic acid. Acetic acid is a preferred among such monocarboxylic acids. Solvents in the form of aqueous solutions thereof, for example about 40 to about 95 wt. % solutions of the acid can be used with good results. Ethanol and other co-solvent materials that oxidize to monocarboxylic acids under the liquid phase oxidation reaction conditions also can be used as is or in combination with monocarboxylic acids. While water is a preferred liquid medium for the process and monocarboxylic acid solvents for the liquid reaction medium are preferred, other suitable solvents or liquid media can be used. According to preferred embodiments of the invention in which the process is conducted in a non-alkaline reaction mixture, examples of liquid media that can be used with or as alternatives to water and $C_1$-$C_8$ monocarboxylic acids, include oxalic acid, malonic acid, methyl malonic acid, dimethyl malonic acid, succinic acid, methyl succinic acid, glutaric acid and cyanoalkanes or cyanoarenes, for example, acetonitrile or benzonitrile, respectively, and including aqueous forms thereof and combinations of two or more thereof may be suitable. Catalysts used for liquid phase oxidations according to the invention comprise palladium, a Group 15 element selected from antimony, bismuth or a combination thereof and at least one Group 4, 5, 6 or 14 metal or metalloid components as described above. Preferred catalysts in some embodiments of the invention are soluble in the liquid phase reaction mixture used for oxidation because soluble catalysts promote contact among catalyst, oxygen gas and liquid feed materials; however, in other preferred embodiments, catalytic compositions in heterogeneous form or in which one or more heterogeneous components is present are used. Catalysts compositions or components thereof that are used in heterogeneous form can be supported or unsupported.

In preferred embodiments, liquid phase oxidation according to the invention is carried out in the absence or substantial absence of active bromine. Although minor amounts of bromine do not appear to hinder catalyst performance, the invented catalysts are active and selective without bromine and, in at least some embodiments, tend to become less active or selectivities shift from more to less fully oxidized aromatic carboxylic acid derivatives with increasing bromine levels. In preferred processes according to the invention, reactive bromine content of the liquid reaction mixture is no more than about 50 ppm by weight of the reaction medium. Minor amounts of reactive bromine that do not have substantial adverse affects on catalyst performance may be tolerated but the reaction system most preferably is free of reactive bromine due to its and its by-products' corrosivity.

Reactants for the liquid phase reaction of the oxidation step also include a source of molecular oxygen. Gaseous oxygen sources are preferred, with air conveniently used as such a source. Oxygen-enriched air, pure oxygen and other gaseous mixtures comprising molecular oxygen also are useful.

Proportions of aromatic feed material, catalyst, oxygen and liquid reaction medium or solvent are not critical and can be varied widely based on factors that include choice of reactants, liquid medium or solvent and catalyst compositions and intended oxidized and aromatic carboxylic acid products, details of process design and operating factors. Solvent or liquid reaction medium to aromatic feedstock weight ratios ranging from about 1:1 to about 30:1 are preferred, with about 2:1 to about 5:1 being more preferred although higher and lower ratios, even in the range of hundreds to one also can be used. Oxygen typically is used in at least a stoichiometric amount based on aromatic feed material but, in the case of gaseous oxygen, not so great, taking into account reactant and solvent compositions, reaction conditions and rates, that off-gases generated as a result of the liquid phase oxidation form a flammable mixture. Oxygen, most commonly supplied in the form of air, is preferably supplied at a rate effective to provide at least about 3 to about 5.6 moles molecular oxygen per mole of aromatic hydrocarbon feed material. Catalyst is used in amounts effective for conversion of aromatic feed material to oxidized product and can vary widely. Other things being equal, reaction rates and consumption of oxygen gas in oxidations using the invented catalytic compositions increase with increased concentrations of the catalytic composition in the oxidation reaction mixture. In batch and continuous slurry processes, the invented catalytic compositions preferably are used in amounts such that concentrations of total catalyst metals and metalloids, based on weight of liquid medium or solvent used in oxidation, are at least about 100 ppmw, and more preferably at least about 500 ppmw, up to about 10,000 ppmw, more preferably up to about 6,000 ppmw, and still more preferably up to about 3,000 ppmw. In continuous flow processes such as fixed, fluid and ebullated bed processes, weight hourly space velocities of substituted aromatic hydrocarbon feed per weight of catalyst composition can be determined by routine experimentation based on catalyst performance reported the in batch and semi-continuous oxidations according to the Examples appearing herein.

Liquid phase reactions for oxidation of aromatic feed material to oxidized products comprising one or more carboxylic acid-substituted aromatic derivatives are conducted in a suitable oxidation reaction zone, which normally comprises one or more reaction vessels. Suitable reaction vessels are configured and constructed to withstand the high temperature and pressure conditions and generally acidic liquid phase reaction mixture present in the reaction zone and to provide for addition and mixing of catalyst, liquid and gaseous reactants and reaction media or solvent and removal of oxidized product or a liquid effluent comprising such product for recovery thereof. Oxidations according to the invention in some of its embodiments tend to be exothermic and, in such cases, heat of reaction can conveniently be controlled by evaporating a reaction off-gas from the liquid reaction mixture and removing the off-gas from the reaction zone. In such cases, the reaction vessel also should be configured for venting of off-gas. Reactor types which can be used include slurry, continuous stirred tank reactors, bubble column reactors, tubular reactors, ebullating bed, fixed or packed bed and trickle bed reactors. Stirred tank reactors in the form of a columnar vessel, normally with a central axis which extends vertically when the vessel is positioned for use, having one or more mixing features for mixing reactants, including distributing gaseous reactants or reactant sources, if used, within the liquid phase boiling reaction mixture. Typically, the mixing feature comprises one or more impellers mounted on a rotatable or otherwise movable shaft. For example, impellers may extend from a rotatable central vertical shaft. Reactors may be constructed of materials designed to withstand the particular temperatures, pressures and reaction compounds used. For use of the invented catalytic compositions in heterogeneous form, fixed, fluidized and ebullated bed reactors and slurry reactors are useful. Stainless or duplex steels are preferred materials of construction for oxidations conducted without sources of reactive bromine although more corrosion-resistant metals or alloys, such as titanium or high nickel steel alloys can be used if desired.

A reaction mixture for the liquid phase oxidation is formed by combining components comprising aromatic feed material, liquid reaction medium or solvent and the catalytic composition according to the invention or components thereof and adding a suitable oxygen source to the mixture. In continuous or semi-continuous processes, components can be combined in one or more mixing vessels before being introduced to the oxidation zone; however, the reaction mixture can also be formed in the oxidation zone. As noted above, in oxidations using water as liquid medium for the reaction mixture, water generated as by-product of the oxidation can serve as the liquid media such that addition thereof from external sources is eliminated or reduced.

Contacting aromatic feed material with oxygen in the presence of catalytic composition according to the invention is conducted under reaction conditions effective for conversion of substituted aromatic compounds having oxidizable substituents to oxidized product comprising aromatic carboxylic acid derivatives of the substituted aromatic feed materials. Preferred reaction conditions include temperatures and pressures effective for such conversion while maintaining a liquid phase reaction mixture. Temperatures of about 100 to about 3000 are preferred. Preferred temperatures are about 140° C., and more preferably about 160° C., to about 230° C., and more preferably about 200° C. Pressure of the liquid phase reaction mixture can be used to control the temperature at which the liquid phase reaction mixture boils and is preferably selected to maintain a substantial liquid phase reaction mixture. Pressures of about 5 to about 40 kg/cm$^2$ gauge are preferred, with preferred pressures for particular processes varying with feed and solvent or liquid reaction media compositions, temperatures and other factors and more preferably ranging between about 10 to about 30 kg/cm$^2$. Residence times in the reaction vessel or reaction zone can be varied as appropriate for given throughputs and conditions, with about 20 to about 150 minutes being generally suited to a range of processes. As will be appreciated by persons skilled in the manufacture of aromatic carboxylic acids, preferred conditions and operating parameters vary with different products and processes and can vary within or even beyond the ranges specified above.

Products obtained by oxidation of aromatic feed materials according to the invention include aromatic carboxylic acid derivatives of the aromatic feed material as well as less fully oxidized derivatives. By way of example, in the oxidation of para-xylene in aqueous acetic acid reaction solvent or water according to the invention, an oxidized product typically includes one or more para-xylene derivatives having at least one carboxylic acid substituent group having an alpha carbon atom, such as terephthalic acid, 4-carboxybenzldehyde, p-toluic acid and p-hydroxymethylbenzoic acid, as well as one or more other oxidation products such as p-tolualdehyde, trimellitic acid, benzoic acid and 2,4',5 5-tricarboxybiphenyl. In embodiments of the invention in which a vapor phase is evaporated from the liquid reaction mixture for control of reaction temperature, major components of the vapor phase typically include water, which is generated as by-product of oxidation of the substituted aromatic feed material and may also be present as liquid medium for the reaction or a component thereof. The vapor phase will also include organic acid reaction solvent and oxidation by-products thereof if an organic acid solvent is used in the process. The vapor phase also typically contains lesser amounts of carbon monoxide and carbon dioxide, which can result from burning of aromatic feed material and, if present, organic acid reaction solvent. Aggregate carbon oxide ($CO$ and $CO_2$) content of the vapor phase preferably is less than about 0.1 mole, and more preferably less than about 0.05 mole carbon oxides per mole of oxygen consumed in oxidation. The vapor phase may also contain minor amounts of unreacted aromatic feed material and oxidation products thereof and unreacted oxygen from gaseous oxygen sources together with inert gas components that may be included in such sources. In preferred embodiments of the invention, aromatic feed material is converted to an oxidation product comprising one or more aromatic carboxylic acid derivatives of the feed material without substantial generation of carbon oxides. More preferably, carbon oxide levels in vent gases from the oxidation, including carbon oxides from burned aromatic feedstock as well as burned organic acid reaction solvent if used, are less than about one-half mole per mole of substituted aromatic feed material and still more preferably less than about 0.25 mole of carbon monoxide plus carbon dioxide per mole of the substituted aromatic feed material.

Oxidized product resulting from the invented process commonly is formed dissolved or as suspended solids in the liquid phase reaction mixture. Recovery of oxidized product or components thereof can be accomplished by any suitable technique. Solid product can be recovered from the liquid reaction medium by filtration techniques. Oxidized products present in the reaction medium both in solution and as suspended solids can conveniently be recovered by crystallization techniques. Aromatic carboxylic acid derivatives of the feed material are preferably recovered in solid form by crystallization from the reaction medium, which can be accomplished conveniently by cooling and releasing pressure on the liquid reaction mixture in the reaction zone or after removal therefrom. Solid product slurried in the liquid and/or solids crystallized from reaction liquid or from crystallization solvents are conveniently separated from the liquids by centrifuging, filtration or combinations thereof. Solid products recovered from the reaction liquid by such techniques comprise aromatic carboxylic acid derivatives of the aromatic feed material and other components of the oxidation product. If needed or desired, further separation of product species can be conducted by any suitable technique, such as extraction with suitable solvents, distillation or sublimation.

In some of its embodiments, features of the invented catalytic compositions and process, such as high conversions and carboxylic acid-selectivities, low carbon oxide generation, and performance even using water as a liquid reaction medium or solvents with relatively high water contents and in the complete or substantial absence of bromine, are especially suited to oxidation of aromatic feed materials comprising at least one dialkyl benzene, intermediate oxidation product thereof or combination thereof to aromatic carboxylic acids in high yields and at high selectivities to benzenedicarboxylic acids. Preferred processes according to such aspects of the invention comprise oxidation of aromatic feed materials comprising para-xylene or one or more intermediate oxidation products thereof or combinations thereof, to an oxidation product comprising terephthalic acid and oxidation of meta-xylene or one or more intermediate oxidation products thereof or combinations thereof to an oxidation products comprising isophthalic acid.

In such embodiments, the oxidation preferably comprises contacting the aromatic feed material with oxygen gas in a liquid phase reaction mixture which comprises water or water and acetic acid and has dissolved or slurried therein, or is otherwise contacted, such as in a fixed bed of supported or unsupported catalyst or catalyst component particles, with, a catalytic composition according to the invention at elevated temperature and pressure effective to maintain a liquid phase reaction mixture and preferably at a temperature of at least about 150 to about 230° C. Catalytic compositions according to the invention that are preferred for such processes exhibit conversions to oxidized product of at least about 80 mole % with selectivities to benzenedicarboxylic acid derivatives of the aromatic feed material of at least about 80% and more preferably with one or both of conversion and aromatic dicarboxylic acid selectivity of at least about 90%.

A particularly preferred catalytic composition according to the invention for such a process with good conversion and selectivity but low generation of carbon oxides from the aromatic feed material comprises at least one palladium component, an antimony component and a tin or molybdenum component or a combination thereof.

Particularly preferred homogeneous catalytic compositions are those comprising components as described above in the form of a solution in water, acetic acid or aqueous acetic acid. Particularly preferred heterogeneous forms of the catalysts for such processes comprise at least a palladium component, and preferably one or more of the antimony, bismuth, and Group 4, 5, 6 or 14 metal and/or metalloid components, and most preferably the palladium and other such components, in solid form or deposited on a support.

Conversion to oxidized aromatic derivatives of the feed material, selectivity of the conversion to aromatic carboxylic acid derivatives and minimal loss of aromatic feed to carbon oxides are achieved using such catalysts in the absence of reactive bromine sources and accordingly the compositions and their components and the oxidation reaction mixture in which they are used are most preferably free of reactive bromine.

Oxidation products of the liquid phase reaction in processes according to this embodiment of the invention comprise terephthalic acid or isophthalic acid in good yield and with intermediate oxidation products and catalyst residues comprising palladium, a Group 15 metal or metalloid selected from antimony, bismuth and combinations thereof, and at least one Group 4, 5, 6 or 14 metal or metalloids present in sufficiently low levels that the oxidation product is useful for conversion to pure forms of terephthalic acid or isophthalic acid if not for conversion directly to polyester suitable for melt spinning into fiber. A preferred terephthalic acid composition according to the invention comprises terephthalic acid and, by weight thereof, about 0.1 to about 500 ppmw palladium, calculated as the element, and about 0.1 to about 500 ppmw antimony, bismuth or combination thereof, calculated as elements, and about 0.1 to about 500 ppmw of a Group 4, 5, 6 or 14 metal or metalloid, calculated as the element, or a combination thereof. A terephthalic acid composition according to a preferred embodiment of the invention comprises terephthalic acid and, by weight thereof, about 0.1 to about 100 ppmw palladium, calculated as the element, and about 0.1 to about 100 ppmw antimony, bismuth or combination thereof, calculated as elements, and about 0.1 to about 100 ppmw of Group 4, 5, 6 or 14 metal or metalloid, calculated as elements, or combination thereof, and especially molybdenum, tin or a combination thereof, Pure forms of aromatic carboxylic acids produced according to the invention can be obtained, if purification is desired, by subjecting the oxidation product, either before or after recovery from the liquid phase reaction mixture, to lower temperature oxidation in one or more stages, such as described in as known from U.S. Pat. Nos. 4,877,900, 4,772, 748 and 4,286,101. Preferred pure forms of terephthalic acid or isophthalic acid with lower impurities contents, such as purified terephthalic acid or "PTA", can made by catalytic hydrogenation of aqueous solutions of the oxidation product in the presence of a noble metal catalyst as described in U.S. Pat. No. 3,584,039. A preferred terephthalic acid composition according to the invention that is suitable for direct conversion by reaction with at least one glycol to polyester suitable for manufacture of fiber comprises terephthalic acid and, by weight thereof, less than about 100 ppmw 4-carboxybzaldehyde and about 0.01 to about 100 ppmw palladium, calculated as the element, and about 0.01 to about 100 ppmw antimony and about 0.01 to about 100 ppmw titanium, vanadium, molybdenum, calculated as the element, or a combination thereof.

The invention is described further in the following examples which are presented for purposes of non-limiting illustration and explanation.

Examples 1-2

Weighed amounts of palladium(II) acetate, antimony(III) acetate and tin(II) acetate salts or stock solutions were measured into a 10 mL Teflon reaction tube together with amounts of para-xylene, acetic acid and water (95 wt % acetic acid and 5 wt % water by weight of the combination thereof) providing a total liquid volume of 7.5 mL. A Teflon stir bar was inserted into the reaction tube and the reaction tube was placed into a thermostatted reactor block. The reactor block was closed, sealing the reaction tube. Headspace in the reaction tube was purged with nitrogen under pressure of 14 bars. The reactor block was used to heat the reaction tube to 170° C., after which air flow into the reaction tube at 1.8 L/min and mixing at 1000 rpm were begun. After 60 minutes, stirring and air flow were stopped and the reactor block and reaction tube were allowed to cool to room temperature. Contents of the reaction tube were removed and dissolved in dimethyl sulfoxide. Samples were analyzed for major product intermediates and impurities by high pressure liquid chromatography (HPLC).

Following the same procedure, para-xylene oxidations were conducted using weighed amounts of palladium(II) acetate and antimony(III) acetate in Control 1, palladium(II) acetate and tin(II) acetate in Control 2 and antimony (III) acetate and tin(II) acetate in Control 3.

Conditions and results of the oxidations are reported in TABLE 1. Amounts of metals and metalloids used in the oxidations are expressed in parts per million by weight of the acetic acid and water used in the oxidations. Conversions reported in the table are expressed as moles of converted para-xylene ("PX") per mole of para-xylene starting material reduced by para-xylene contents of condensed overhead vapors from the oxidations, which typically ranged up to 5% of the initial charge. Selectivities shown in the table are percentages, by weight, of terephthalic acid ("TA"), 4-carboxybenzaldehyde ("4CBA") and p-toluic acid ("PTOL"), respectively, of the converted products.

TABLE 1

| | Run No. | | | | |
|---|---|---|---|---|---|
| | Control 1 | Control 2 | Control 3 | Example 1 | Example 2 |
| Composition | Pd/Sb | Pd/Sn | Sb/Sn | Pd/Sb/Sn | Pd/Sb/Sn |
| Pd (ppmw) | 504.7 | 510.9 | — | 483.0 | 510.6 |
| Sb (ppmw) | 513.2 | — | 485.5 | 503.7 | 494.5 |
| Sn (ppmw) | — | 503.6 | 496.5 | 493.9 | 489.2 |
| Temperature (° C.) | 167 | 169 | 168 | 168 | 147 |
| PX Conversion (mole %) | 8.20 | 10.88 | 0.04 | 94.67 | 78.98 |
| Selectivity (% converted product) | | | | | |
| TA | 0.00 | 6.13 | 0.00 | 2.70 | 4.04 |
| 4CBA | 0.47 | 6.24 | 0.00 | 3.67 | 4.25 |
| PTOL | 76.75 | 65.60 | 0.00 | 77.58 | 72.04 |

As seen from the table, conversions of para-xylene to carboxylic acid derivatives using binary combinations of palladium with tin or antimony without bromine in Controls 1 and 2 were far greater than that with tin and antimony in Control 3. Conversions in Controls 1 and 2 were also significantly greater than those in trials using each of palladium, antimony and tin alone in Controls 11-13 reported below. Surprisingly, the catalytic compositions used in Examples 1 and 2, which contained palladium, antimony and tin, showed far greater conversion of the para-xylene feed to carboxylic acid derivatives, including nearly quantitative conversion in Example 3, in combination with low levels of carbon oxides.

Example 3

Weighed amounts of palladium(II) acetate, antimony(III) acetate and tin(II) acetate were added to a solvent composed of 95 wt. % acetic acid and 5 wt. % water and the resulting mixture was batch loaded into a stirred 100 mL titanium reactor. The reactor was sealed, pressurized to 22 bara with compressed nitrogen and heated to about 190-195° C. and, while maintaining those conditions, a gaseous mixture of 8 vol. % oxygen with nitrogen was added continuously at a rate of 1.0 gram/minute and greater than 99 wt % pure para-xylene was added continuously at a rate of 0.133 gram/minute. After one hour, addition of para-xylene feed was stopped. Addition of the gaseous mixture was continued for an additional thirty minutes and then stopped. Vent gas removed from the reactor was sampled at intervals beginning after thirty minutes of para-xylene addition. The reactor contents were then cooled and a sample of product slurry resulting from the reaction was removed and analyzed by HPLC. TABLE 2 reports metals concentrations, yields of products determined by HPLC and carbon oxide production calculated from vent gas samples.

TABLE 2

| Catalyst Metals or Metalloids | Concentration (ppmw) |
|---|---|
| Palladium | 8000 |
| Antimony | 7999 |
| Tin | 5337 |
| Products | Yield (mole/mole para-xylene fed × 100%) |
| TA | 50.3 |
| 4CBA | 6.4 |
| PTOL | 6.2 |
| p-Tolualdehyde ("PTAL") | 7.2 |
| Carbon Oxides | 19 |

From Example 3 and TABLE 2 it is evident that the palladium-antimony-tin composition of the example was active in the absence of bromine for conversion of para-xylene to derivatives with oxidized substituent groups at a yield of about 70 mole % based on moles of para-xylene feed. Selectivity to carboxyl-substituted derivatives of the p-xylene feed was high, as seen not only from the 62.9% combined yields of TA, 4CBA and PTOL, each of which includes at least one carboxyl-substituent, but also from the 50.3% yield of TA. The 50.3% TA yield based on para-xylene feed corresponds to about 72% based on moles of para-xylene feed converted to oxidized alkyl aromatic derivatives. TA selectivity of the catalytic composition of Example 3 at the reaction temperature of the example was unexpected. Also as seen from the example and the table, good oxidized alkyl aromatic yield and carboxyl selectivity with the palladium-antimony-tin catalyst were achieved with carbon oxides generated in an amount corresponding to only 19% of the molar amount of p-xylene added.

Controls 4-12

For purposes of comparison a bromine-promoted cobalt-manganese catalyst representative of catalysts used in commercial manufacture of terephthalic acid by oxidation of para-xylene was tested in Control 4. Bromine-free catalysts containing various amounts of cobalt and zirconium as in US Patent Application No. 2002/0188155 were used in Controls 5-12.

For Control 4, cobalt(II) acetate tetrahydrate, manganese (II) acetate tetrahydrate and a solution of 48 wt % hydrobromic acid in water were added to a solvent containing 95 wt % acetic acid and 5 wt % water in amounts providing 615 parts per million by weight ("ppmw") cobalt, 616 ppmw manganese and 1120 ppmw bromine. The solution was loaded into a stirred 100 mL titanium reactor. The reactor was sealed, pressurized to 22 bara with compressed nitrogen and heated to maintain a constant reactor temperature of 190° C. and, while maintaining those conditions, a gaseous mixture of 8 vol. % oxygen and 92 vol % nitrogen was added continuously at a rate of 2.0 grams/minute and para-xylene (>99% pure) was added continuously at a rate of 0.133 gram/minute. After one hour, addition of para-xylene feed was stopped. Addition of the gaseous mixture was continued for an additional thirty minutes and then stopped. The reactor contents were then cooled and a sample of the total reactor product slurry was removed and analyzed by HPLC. Production of carbon oxides during the reaction was calculated based on concentrations in gas samples removed from the reactor during the last 30 minutes of para-xylene addition.

For controls 5-12, cobalt(II) acetate tetrahydrate and a solution of 16.2 wt % zirconyl(IV) acetate in water were added to an acetic acid and water solvent as in Control 4 in amounts providing varying levels of cobalt and zirconium. The resulting catalysts were loaded into a reactor as used in Control 4 and, while maintaining the reactor at a constant temperature of 195° C. and pressure of 22 bara, a nitrogen and oxygen mixture and para-xylene feed, both as in Control 4, were added continuously over a period of one hour at rates of 2.0 g/min. of the gas mixture and 0.133 g/min. of the para-xylene. Addition of para-xylene feed was discontinued after one hour and addition of the oxygen and nitrogen gas mixture was discontinued after another one-half hour. Reactor contents were then cooled and total product was analyzed as in Control 4. Carbon oxide production was calculated from vent gas samples taken during the last 30 minutes of p-xylene addition.

Results of the oxidations with Controls 4-12 are reported in TABLE 3, in which numbers of the Controls are shown in the "#" column.

TABLE 3

| # | Catalyst Metals and Br Proportions (ppmw) | Yields (mole/mole p-xylene fed × 100%) | | | | |
|---|---|---|---|---|---|---|
| | | TA | 4CBA | PTOL | PTAL | COx |
| 4 | Co/Mn/Br 615/615/1120 | 98.1 | 0.4 | 0.4 | 0.2 | 35 |
| 5 | Co/Zr 500/50 | 9.2 | 4.9 | 49.5 | 3.9 | 131 |
| 6 | Co/Zr 5000/4975 | 4.9 | 2.1 | 39.2 | 7.8 | 189 |
| 7 | Co/Zr 500/4975 | 6.8 | 2.1 | 45.6 | 4.3 | 119 |
| 8 | Co/Zr 5000/4975 | 5.6 | 2.1 | 39.0 | 6.1 | 193 |
| 9 | Co/Zr 5000/50 | 4.9 | 1.9 | 36.9 | 4.8 | 172 |
| 10 | Co/Zr 500/50 | 9.9 | 2.0 | 48.0 | 3.0 | 103 |
| 11 | Co/Zr 500/498 | 9.7 | 2.4 | 48.6 | 3.8 | 146 |
| 12 | Co/Zr 5000/498 | 5.3 | 2.1 | 37.8 | 7.8 | 204 |

From TABLE 3, it can be seen that the conventional, bromine-promoted cobalt and manganese catalyst of Control 4 was highly selective to TA with only minor production of less fully oxidized intermediates. PTOL, which is an intermediate oxidation product in oxidation of para-xylene to terephthalic acid, was the primary oxidation product produced in the bromine-free cobalt-zirconium catalyzed trials in Controls 5-12. It also can be seen that carbon oxide generation with the cobalt-zirconium-catalyzed controls was very high.

Controls 13-23

Weighed amounts of each of palladium(II) acetate, antimony(III) acetate and tin(II) acetate, bismuth (III) acetate and molybdenum(II) acetate dimer were added to a solvent composed of 95 wt. % acetic acid and 5 wt. % water and the resulting mixtures were batch loaded individually and in various combinations into a stirred, vented 300 mL titanium reactor. The reactor was sealed, pressurized to 390 psig with nitrogen and agitation was begun. The reactor contents were heated to 182° C., after which the nitrogen flow was replaced by a mixture of 8 vol. % oxygen in nitrogen flowing at 15 standard cubic feet per hour ("SCFH"), and para-xylene feedstock and supplemental solvent were added. The feedstock and supplemental solvent were added for 60 minutes at 0.567 mL/min and 0.633 mL/min, respectively. Thirty seconds after the reactor contents had reached 182° C., the temperature set-point was increased to 194° C. and after another 20 minutes the set-point temperature was increased to 195° C. After 60 minutes, feedstock and solvent additions were terminated. For 30 minutes thereafter the 8% oxygen in nitrogen gas mixture was added at 15 SCFH. At the end of the 30 minutes, the flow of 8% oxygen in nitrogen was replaced by a flow of only nitrogen gas. The vent gas from the reactor was monitored continuously by a bank of on-line analyzers for carbon monoxide, carbon dioxide, and oxygen throughout span of the oxidation. The heating mantel was then removed and the reactor was cooled, depressurized, and unsealed. A representative sample of the reactor effluent was removed for analysis by HPLC. Results of the oxidations are reported in TABLE 4. Conversions reported in the table are expressed as moles of converted para-xylene per mole of para-xylene starting material. Selectivities shown in the table are percentages, by weight, of terephthalic acid ("TA"), 4-carboxybenzaldehyde ("4CBA"), p-toluic acid ("PTOL") and p-tolualdehyde ("PTOL") respectively, of the converted products weight. Acid Selectivity reported in the Table is the sum of TA, 4CBA and PTOL selectivities. Carbon oxides production was calculated from vent gas samples.

TABLE 4

| | Control # | | | | |
|---|---|---|---|---|---|
| | 13 | 14 | 15 | 16 | 17 |
| Metal | Pd | Sb | Sn | Bi | Mo |
| Conc (ppmw) | 4000 | 4570 | 4460 | 3600 | 7845 |
| Selectivity (%) | | | | | |
| TA | 2.06 | 8.69 | 3.21 | 6.03 | 4.03 |
| 4-CBA | 3.92 | 1.75 | 2.54 | 2.00 | 2.15 |
| PTOL | 5.04 | 20.90 | 48.32 | 40.14 | 29.88 |
| PTAL | 52.27 | 67.42 | 44.61 | 50.08 | 61.95 |
| Burned pX (%) | 6.7 | 1.23 | 1.33 | 1.75 | 1.99 |
| pX Conversion (%) | 4.67 | 1.18 | 2.09 | 1.05 | 2.10 |
| Acid Selectivity (%) | 11.02 | 31.34 | 54.07 | 48.17 | 36.16 |
| COx (moles) | 0.015 | 0.001 | 0.001 | 0.001 | 0.002 |
| $O_2$ Consumed (moles) | 0.129 | 0.083 | 0.0098 | 0.089 | 0.100 |
| COx/pX (mol/mol) | 0.056 | 0.002 | 0.005 | 0.003 | 0.007 |
| COx/$O_2$ * 100 | 11.61 | 0.792 | 1.280 | 0.938 | 1.902 |

Combinations of salt solutions used in Controls 13-17 were used in para-xylene oxidations and reactor liquid product and vent gas samples were analyzed. Results are reported in TABLE 5.

As seen from TABLE 6, oxidations with vanadium and titanium were comparable to those with the individual metals and metalloids in Controls 13-23. The combination of titanium and vanadium in Control 26 was better than the individual metals but, as with the binary combinations in Controls 18-23, did not approach the conventional, bromine-promoted cobalt-manganese catalyst of Control 4 or the palladium, antimony, tin composition in Examples 1-3.

TABLE 5

| | Run | | | | | |
|---|---|---|---|---|---|---|
| | Control 18 | Control 19 | Control 20 | Control 21 | Control 22 | Control 23 |
| Catalyst | Pd/Sn | Sb/Sn | Pd/Sb | Pd/Bi | Pd/Mo | Sb/Mo |
| Conc (ppmw) | 4000/2000 | 2000/2000 | 4000/2000 | 4000/3400 | 4000/5000 | 2000/2000 |
| Products Sel (%) | | | | | | |
| TA | 4.51 | 66.80 | 12.90 | 5.64 | 10.60 | 23.83 |
| 4-CBA | 3.05 | 2.25 | 19.07 | 1.28 | 4.82 | 3.37 |
| PTOL | 32.68 | 14.87 | 42.23 | 28.97 | 37.97 | 24.60 |
| PTAL | 45.41 | 16.08 | 25.33 | 61.87 | 30.16 | 40.98 |
| Burned pX | 14.35 | <0.001 | 0.47 | 2.23 | 16.46 | 7.23 |
| % pX Conversion | 6.49 | 3.08 | 19.92 | 9.13 | 6.29 | 0.53 |
| Acid Selectivity (%) | 40.24 | 83.92 | 74.20 | 35.89 | 53.39 | 51.80 |
| COx (moles) | 0.049 | <0.001 | 0.010 | 0.009 | 0.055 | 0.002 |
| $O_2$ Con-sumed (moles) | 0.189 | 0.081 | 0.477 | 0.128 | 0.215 | 0.085 |
| COx/pX (mol/mol) | 0.180 | <0.001 | 0.036 | 0.035 | 0.205 | 0.007 |
| COx/$O_2$ * 100 | 25.599 | <0.001 | 2.271 | 7.057 | 25.617 | 2.145 |

Comparing TABLES 3-5, it is evident that none of the metals of Controls 13-23 approached the performance of the bromine-promoted cobalt and manganese catalyst of Control 1 or the combination of palladium, antimony and tin in Examples 1-3. Although metals concentration in Control 19, using a combination of antimony and tin, was about 4 times that in Control 3, also using antimony and tin, conversion was still low.

Controls 24-26

Oxidations were conducted as in Controls 13-23 using weighed amounts of vanadium(III) acetylacetonate and titanium(IV) oxide acetylacetonate in aqueous 95 wt. % acetic acid solvent. Results are reported in TABLE 6.

TABLE 6

| | Control No. | | |
|---|---|---|---|
| | Control 24 | Control 25 | Control 26 |
| Metal | V | Ti | V/Ti |
| Conc (ppmw) | 2000 | 2000 | 2000/2000 |
| Selectivity (%) | | | |
| TA | 8.82 | 3.28 | 23.30 |
| 4-CBA | 0.54 | 0.31 | 0.57 |
| PTOL | 18.20 | 24.30 | 13.42 |
| PTAL | 54.04 | 56.54 | 46.17 |
| Acid Selectivity (%) | 27.56 | 27.89 | 37.29 |
| Burned pX (%) | 18.40 | 15.57 | 7.56 |
| pX Conversion (%) | 4.12 | 3.67 | 16.54 |
| COx (moles) | 0.043 | 0.031 | 0.069 |
| O2 Consumed (moles) | 0.164 | 0.131 | 0.210 |
| COx/pX (mol/mol) | 0.153 | 0.112 | 0.247 |
| COx/O2 * 100 | 25.91 | 23.84 | 32.69 |

Examples 4-11

In these examples palladium-antimony-tin compositions according to the invention were used for semi-continuous oxidations of various feed materials using a 300 mL titanium Parr reactor outfitted with a Magnadrive impeller agitator, reflux condensers, a back pressure regulator, a mass flow controller, on-line vent gas analyzers (CO, $O_2$, and $CO_2$), one pump for adding liquid feedstock and another pump for adding supplemental solvent.

The reactor bottom was preloaded with weighed amounts of palladium(II) acetate (1.208 g), antimony(III) acetate (1.407 g), and tin(II) acetate (1.143 g), and 95% aqueous acetic acid (72.6 g). The reactor was sealed, pressurized to 390 psig with nitrogen and agitation was begun. The reactor contents were heated to 182° C. At initiation, the nitrogen flow was replaced by a mixture of 8% oxygen in nitrogen flowing at 15 standard cubic feet per hour ("SCFH"), and the feedstock and supplemental solvent were added. The feedstock and the aqueous, 95 wt % acetic acid as supplemental solvent were added for 60 minutes at 0.567 mL/min and 0.633 mL/min, respectively. Thirty seconds after initiation, the temperature set-point was increased to 194° C. Twenty minutes after initiation, the set-point temperature was increased again to 195° C. After 60 minutes, feedstock and solvent additions were terminated and, in each of Examples 4-6, a 30 minute tailout period was begun. During that period, the 8% oxygen in nitrogen gas mixture was added at 15 SCFH. At the end of the tailout period, the flow of 8% oxygen in nitrogen was replaced by a flow of only nitrogen gas. Example 7 was carried out as in Examples 4-6 except the tailout step was omitted. In all examples, the reactor was sequentially removed from the heat source, cooled, depressurized, and unsealed. Representative samples of the total reactor product slurries were collected and analyzed by HPLC and Karl Fisher (water) analyses.

Results of Examples 4-7 are reported in TABLE 7.

TABLE 7

| | Example: | | | | |
|---|---|---|---|---|---|
| | 4 | 5 | 6 | Ave. 4-6 | 7 |
| Feed: | Para-Xylene (PX) | | | | |
| Products Sel (%) | | | | | |
| TA | 80.37 | 83.25 | 81.48 | 81.70 | 78.57 |
| 4CBA | 11.04 | 9.21 | 10.65 | 10.30 | 14.24 |
| PTOL | 4.14 | 3.48 | 3.63 | 3.75 | 4.16 |
| PTAL | 0.83 | 0.71 | 0.76 | 0.77 | 3.01 |
| Burned pX | 3.63 | 3.35 | 3.48 | 3.49 | 0.02 |
| pX Conversion (mol %) | 50.78 | 57.78 | 54.98 | 54.52 | 28.07 |
| Trimellitic Acid (TMLA) (wt %) | 0.2045 | 0.2070 | 0.2228 | 0.2114 | 0.0066 |
| Benzoic Acid (BA) (wt %) | 0.1816 | 0.1890 | 0.1972 | 0.1893 | 0.1321 |
| 2,4',5-tricarboxybiphenyl (wt %) | 0.051 | 0.048 | 0.058 | 0.052 | 0.410 |
| Main Oxidation $COx^a$ (mol) | 0.085 | 0.092 | 0.091 | 0.089 | 0.088 |
| Tailout $COx^b$ (mol) | 0.196 | 0.198 | 0.189 | 0.195 | — |
| COx/Feedstock $(mol/mol)^a$ | 0.317 | 0.332 | 0.329 | 0.326 | 0.318 |
| $COx/O_2$ $(mol * 100/mol)^a$ | 10.18 | 10.84 | 10.87 | 10.63 | 10.61 |

$^a$Data collected only over the first 60 minute period of the oxidation.
$^b$Data collected during the tailout period.

The oxidations in Examples 4-6 produced TA in an average selectivity of almost 82%. The average total selectivities of less fully oxidized carboxylic acid derivatives (4CBA+PTOL) in the oxidations using para-xylene feed was 14.05 mole %.

Results of semi-continuous oxidations using alternate feed materials in Examples 8-11 are reported in TABLE 8.

TABLE 8

| | Example: | | | |
|---|---|---|---|---|
| | 8 | 9 | 10 | 11 |
| Feed: | p-Tolualdehyde | | p-Methylacetophenone | |
| Product Sel. (%) | | | | |
| TA | 32.72 | 34.50 | 11.64 | 11.69 |
| 4CBA | 7.43 | 7.70 | 2.65 | 1.97 |
| PTOL | 54.38 | 52.49 | 43.66 | 46.07 |
| PTAL | 2.57 | 2.54 | 1.32 | 0.65 |
| Feedstock Converted (mol %) | 63.74 | 67.65 | 13.03 | 12.80 |
| Burned Feed (mol %) | 2.90 | 2.77 | 40.74 | 39.60 |
| TMLA (wt %) | 0.0708 | 0.0638 | 0.1427 | 0.1562 |
| BA (wt %) | 0.1926 | 0.2041 | 0.0305 | 0.0884 |
| 2,4',5-tricarboxybiphenyl (wt %) | 0.1898 | 0.1544 | 0.4375 | 0.2474 |
| Main Oxidation COx (mol %)$^a$ | 0.091 | 0.090 | 0.367 | 0.345 |
| Tailout Oxidation $COx^b$ | 0.058 | 0.055 | 0.206 | 0.198 |
| COx/Feedstock $(mol/mol)^a$ | 0.317 | 0.321 | 0.639 | 1.396 |
| $COx/O_2$ $(mol*100/mol)^a$ | 21.135 | 20.696 | 57.479 | 53.900 |

$^a$Data collected only over the first 60 minute period of the oxidation.
$^b$Data collected during the tailout period.

TABLE 8 displays oxidation results using liquid feedstocks, p-tolualdehyde and p-methylacetophenone. The duplicate p-tolualdehyde oxidations in Examples 8 and 9 generated very similar results, demonstrating good reproducibility of the oxidations. The p-tolualdehyde feed was converted to TA, although at lower efficiency and with greater levels of partial carboxylic acid derivatives as compared to the para-xylene feed in Examples 4-6. However, the total COx generated was much lower than in the para-xylene oxidations. The p-methylacetophenone oxidations in Examples 10 and 11 had similar results, including low TA yields. The total COx generated in those examples was higher than the amount made in the p-tolualdehyde oxidations, consistent with a higher activity of the catalyst for oxidation of the p-methylacetophenone feed material to carbon oxides than the p-tolualdehyde and p-xylene feeds.

Examples 12-15

Oxidation trials were conducted substantially as in Example 7 using catalyst compositions prepared from aqueous acetic acid solutions of palladium and antimony salts and combinations of bismuth, chromium, vanadium, molybdenum and calcium. Catalyst metals and results of the oxidation trials are reported in TABLE 9.

TABLE 9

| | Example | | | |
|---|---|---|---|---|
| | 12 | 13 | 14 | 15 |
| Catalyst | Pd/Sb/Bi/Mo | Pd/Sb/Cr/Mo | Pd/Sb/V/Mo | Pd/Sb/Mo/Ca |
| Product Sel.(%) | | | | |
| TA | 21.64 | 15.38 | 3.89 | 37.55 |
| 4-CBA | 13.11 | 3.50 | 3.00 | 12.54 |
| p-Toluic Acid | 59.26 | 24.35 | 23.10 | 40.73 |
| p-Tolualdehyde | 5.78 | 56.77 | 51.86 | 4.34 |
| Burned pX | 0.20 | <0.01 | 18.15 | 4.84 |
| Total Int Sel (%) | 78.16 | 84.62 | 77.96 | 57.61 |
| PX Conversion (mol %) | 78.63 | 3.78 | 4.55 | 42.18 |
| Byproducts (wt %) | | | | |
| Benzoic Acid | 0.1310 | 0.0050 | 0.0210 | 0.5600 |
| 2,4',5-Tricarboxybiphenyl | 0.2490 | 0.0041 | 0.0540 | 0.1970 |
| Trimellitic Acid | <0.001 | 0.0050 | 0.0010 | 0.0020 |
| COx (moles) | 0.007 | <0.001 | 0.045 | 0.096 |
| $O_2$ Consumed (moles) | 0.592 | 0.105 | 0.193 | 0.735 |
| COx/pX (mol/mol) | 0.026 | <0.001 | 0.167 | 0.355 |
| $COx/O_2$ * 100 | 1.163 | <0.001 | 23.315 | 13.000 |

Examples 16-19

In these examples palladium-antimony-tin compositions according to the invention were used in batch oxidations of various feed materials in solid form at ambient temperature using the 300 mL reactor used in Examples 4-11. Batch oxidations were conducted by loading the reactor with palladium(II) acetate (1.208 g), antimony(III) acetate (1.407 g), and tin(II) acetate (1.143 g), weighed amounts of solid feed materials and 95% aqueous acetic acid (114.5 g). In Examples 16 and 17, the feed was 42.4 g p-toluic acid and in Examples 18 and 19 the feed was 41.7 g terephthaldehyde. The reactor was sealed, pressurized to 390 psig by addition of nitrogen gas and agitation was started. The reactor contents were heated to 182° C. and the nitrogen flow was replaced by flow of a mixture of oxygen and nitrogen containing 8% oxygen at 15 SCFH. Thirty seconds after initiation, the temperature set-point was increased to 194° C. Twenty minutes after initiation, the temperature set-point was increased to 195° C. After 90 minutes, the 8% oxygen in nitrogen flow was replaced by a flow of only nitrogen. The reactor was removed from the heat source, cooled, depressurized, and unsealed. Representative samples of the total reactor product slurries from each run were collected and analyzed by HPLC and Karl Fisher analyses. Results are reported in TABLE 10.

TABLE 10

| | Example: | | | |
|---|---|---|---|---|
| | 16 | 17 | 18 | 19 |
| Feed: | p-Toluic Acid | | Terephthaldehyde | |
| Product Sel (%) | | | | |
| TA | 11.60 | 0.27 | 55.72 | 58.07 |
| 4CBA | 6.73 | 0.62 | 32.54 | 29.92 |
| PTOL | 81.26 | 99.06 | — | — |
| Burned Feedstock | 0.41 | 0.05 | 11.69 | 11.92 |
| Feedstock Converted (mol %) | 46.10 | <1.00 | 50.88 | 51.24 |
| TMLA (wt %) | 0.0236 | 0.0000 | 0.4905 | 0.4891 |
| BA (wt %) | 0.2224 | 0.0484 | 2.1662 | 2.0064 |
| 2,4',5-tricarboxybiphenyl (wt %) | 0.0478 | 0.0043 | 1.2386 | 0.9192 |
| Total Oxidation COx (mol) | 0.056 | 0.002 | 0.291 | 0.301 |
| COx/Feedstock (mol/mol) | 0.211 | 0.009 | 1.116 | 1.149 |
| COx/O$_2$ (mol * 100/mol) | 24.878 | 2.826 | 52.270 | 52.361 |

Inconsistent results in Examples 16 and 17 appear to have resulted from the presence of a contaminant(s) carried over from a previous oxidation experiment. When the p-toluic acid feed was oxidized a second time as in Example 17, there was very little measured activity. Therefore, Example 17 is believed to represent the more accurate results of p-toluic acid oxidation. Examples 18 and 19 produced reproducible results in oxidation of a terephthaldehyde feed. TA product selectivity averaged about 57% with 4-CBA as the only intermediate carboxylic acid derivative at about 31%. Total COx generated in these examples was high.

Examples 20-21

A palladium, antimony, tin composition according to the invention was used for semi-continuous oxidations according to the procedure of Examples 4-6 except that meta-xylene was used as feed material. Results are reported in TABLE 11. The averages of the results of Examples 4, 5 and 6 as reported in TABLE 7 are also repeated in TABLE 11 for comparison of results with the meta- and para-xylene feeds.

TABLE 11

| | Example: | | | |
|---|---|---|---|---|
| | 20 | 21 | Ave. 4-6 | |
| | Feed: | | | |
| | Meta-Xylene | | Para-Xylene (PX) | |
| Product Sel (%) | (MX) | | Products Sel (%) | |
| Isophthalic Acid (IA) | 56.45 | 55.26 | TA | 81.70 |
| 3CBA | 11.44 | 11.56 | 4-CBA | 10.30 |
| MTOL | 26.36 | 27.22 | PTOL | 3.75 |
| MTAL | 2.35 | 2.67 | PTAL | 0.77 |
| Burned MX | 3.39 | 3.29 | Burned PX | 3.49 |
| MX Conversion (mol %) | 56.77 | 56.40 | PX Conversion (mol %) | 54.52 |
| TMLA (wt %) | 0.2837 | 0.4905 | TMLA (wt %) | 0.2114 |
| BA (wt %) | 0.5662 | 0.5618 | BA (wt %) | 0.1893 |
| 2,3',4-tricarboxybiphenyl (wt %) | 0.0142 | 0.0130 | 2,4',5-tricarboxybiphenyl (wt %) | 0.410 |
| Main Oxidation COx$^a$ | 0.089 | 0.086 | Main Oxidation COx$^a$ | 0.089 |
| Tailout COx$^b$ | 0.231 | 0.226 | Tailout COx$^b$ | 0.195 |
| COx/MX (mol/mol)$^a$ | 0.331 | 0.319 | COx/PX (mol/mol)$^a$ | 0.326 |
| COx/O$_2$ (mol * 100/mol)$^a$ | 11.44 | 11.09 | COx/O$_2$ (mol * 100/mol)$^a$ | 10.63 |

$^a$Data collected over the first 60 minute period of the oxidation.
$^b$Data collected in the tailout period.

The meta-xylene oxidations of Examples 20 and 21 again demonstrated good reproducibility. There was a lower yield of IA than there was of TA in the para-xylene oxidations of Examples 4-6. The lower IA yields were also consistent with the lower conversions of meta-xylene oxidation intermediates such as m-toluic acid. Overall, meta-xylene oxidations in Examples 20 and 21 produced slightly more COx than the para-xylene oxidations of Examples 4-6.

Examples 22-25

Batch oxidations of PX feed were conducted as in Examples 16-19 except that batch initiation temperatures were varied. Pressure was fixed at 390 psig. Results are reported in TABLE 12 with the average of the results from Examples 4-6 repeated from TABLE 7 for reference.

TABLE 12

| | Example | | | | |
|---|---|---|---|---|---|
| | 22 | 23 | 24 | 25 | Ave. 4-6 |
| Initiation Temperature (° C.) | 100 | 120 | 140 | 182 | 182 |
| Product Sel (%) | | | | | |
| TA | 14.56 | 6.08 | 6.70 | 32.16 | 81.70 |
| 4-CBA | 7.74 | 5.80 | 10.47 | 24.08 | 10.30 |
| PTOL | 51.37 | 55.53 | 68.27 | 29.84 | 3.75 |
| PTAL | 26.33 | 30.12 | 13.11 | 8.33 | 0.77 |
| PX Burned | 0.00 | 2.46 | 1.45 | 5.59 | 3.49 |
| PX Conversion (mol %) | 2.14 | 3.06 | 8.63 | 31.09 | 54.52 |

TABLE 12-continued

|  | Example | | | | |
|---|---|---|---|---|---|
|  | 22 | 23 | 24 | 25 | Ave. 4-6 |
| TMLA (wt %) | <0.0001 | <0.0001 | 0.0021 | 0.0911 | 0.2114 |
| BA (wt %) | <0.0001 | <0.0001 | 0.0414 | 0.3896 | 0.1893 |
| 2,4',5-Tricarboxybiphenyl (wt %) | 0.0339 | 0.0702 | 0.2181 | 0.7432 | 0.052 |
| Main Oxidation COx (mol)[a] | 0.001 | 0.004 | 0.021 | 0.092 | 0.089 |
| Tailout Oxidation COx (mol)[b] | — | — | — | — | 0.195 |
| COx/Feedstock (mol/mol)[a] | 0.005 | 0.013 | 0.074 | 0.329 | 0.326 |
| COx/$O_2$ (mol * 100/mol)[a] | 3.08 | 5.28 | 4.451 | 13.11 | 10.63 |

[a]Data collected during the first 60 minute period of oxidation.
[b]Data collected during the tailout period.
[c]Batch oxidation time was limited to 55 minutes.

Oxidation activities were low until a temperature of 140° C. was employed in Example 24. Unexpectedly, at 140° C. there was very little burning of solvent to carbon oxides for the degree of PX conversion that was achieved. When the oxidation was repeated, but at a temperature of 182° C. in Example 25, TA yield nearly doubled. At the higher temperature in Example 25, however, total carbon oxides formation was higher.

Controls 27-28

Semi-continuous oxidations without tailouts were conducted as in Example 7 but with addition of 48 wt % aqueous hydrobromic acid, which is a common bromine source used as a promoter in commercial manufacture of terephthalic acid by cobalt-manganese-catalyzed oxidation of para-xylene. Results are reported in TABLE 13, with results from Example 7 also included for reference.

TABLE 13

|  | Run: | | |
|---|---|---|---|
|  | Example 7 | Control 27 | Control 28 |
| HBr (g 48 wt % aqueous) | 0.000 | 0.0777 | 0.1540 |
| Product Sel (%) |  |  |  |
| TA | 78.57 | 8.66 | 2.36 |
| 4CBA | 14.24 | 3.74 | 0.26 |
| PTOL | 4.16 | 77.09 | 62.28 |
| PTAL | 3.01 | 9.28 | 34.54 |
| Burned pX | 0.02 | 1.24 | 0.56 |
| PX Conversion (mol %) | 28.07 | 39.40 | 7.25 |
| TMLA (wt %) | 0.0066 | 0.0050 | <0.0001 |
| Benzoic Acid (BA) (wt %) | 0.1321 | 0.1083 | <0.0001 |
| 2,4',5-Tricarboxybiphenyl (wt %) | 0.4103 | 0.1409 | <0.0018 |
| Total Oxidation COx (mol) | 0.088 | 0.023 | 0.002 |
| COx/Feedstock (mol/mol) | 0.318 | 0.082 | 0.007 |
| COx/$O_2$ (mol * 100/mol) | 10.61 | 5.176 | 1.517 |

In contrast to Example 7 in which no bromine was added, under otherwise identical conditions the oxidations in Controls 27 and 28 were impeded by the presence of the hydrogen bromide. TA product selectivity fell by an order of magnitude and the main product was PTOL in Control 27. In Control 28, bromine concentration was double that in Control 27 and only a trace of TA was made.

Examples 26-29

A catalyst composition of palladium, tin, antimony and molybdenum was used in a series of semi-continuous para-xylene oxidations conducted substantially as in Controls 13-23 except that in Examples 26-28 the reaction temperatures ranged from 193 to 199° C. Catalyst compositions were prepared by charging weighed amounts of palladium(II) acetate, antimony(III) acetate, tin(II) acetate, molybdenum (II) acetate dimer and 95% aqueous acetic acid to the reactor in amounts providing 4000 ppmw palladium, 2000 ppmw antimony, 2000 ppmw tin and 5000 ppmw molybdenum, calculated as metals and based on weight of aqueous acetic acid. Contents of the reactor were removed after each oxidation run and were analyzed as in Controls 13-23 to assess products and selectivities. Results of Examples 26-28, together with selectivities averaged over the three experiments, are reported in Table 14. Reactor contents from each run also included darkly colored solid particles.

TABLE 14

|  | Example | | | |
|---|---|---|---|---|
|  | 26 | 27 | 28 | Ave. Ex. 26-28 |
| Products Sel (%) |  |  |  |  |
| TA | 95.52 | 94.93 | 95.06 | 95.17 |
| 4CBA | 2.60 | 3.07 | 3.08 | 2.92 |
| PTOL | 0.52 | 0.63 | 0.58 | 0.58 |
| PTAL | 0.29 | 0.38 | 0.37 | 0.35 |
| Burned Feed | 1.07 | 0.99 | 0.91 | 0.99 |
| PX Conversion (mol %) | 92.34 | 85.03 | 85.67 | 87.68 |
| BA | 0.0034 | 0.0038 | 0.0030 | 0.0034 |
| 2,4,'5-tricarboxybiphenyl | 0.0100 | 0.0109 | 0.0074 | 0.0094 |
| TMLA | 0.1727 | 0.1660 | 0.1634 | 0.1674 |
| COx (moles) | 0.043 | 0.039 | 0.036 | 0.039 |
| $O_2$ Consumed (moles) | 0.930 | 0.893 | 0.891 | 0.905 |
| COx/pX (mol/mol) | 0.166 | 0.140 | 0.130 | 0.145 |
| COx/$O_2$ * 100 (mol/mol) | 4.671 | 4.353 | 4.037 | 4.354 |

As seen from these examples and the table, terephthalic acid selectivity of the palladium, tin, antimony and molybdenum containing catalytic composition was exceptionally high and results of the three runs were highly reproducible.

In Example 29, the procedure of Examples 26-28 was followed except that the temperature was increased to 203-209° C. The oxidation proceeded vigorously with even greater selectivity to terephthalic acid (97%) than in Examples 26-28, 1.2% 4CBA and 0.1% each of PTOL and PTAL. Feedstock burning and generation of carbon oxides at the higher temperature were about 1.5-2 times the average of Examples 26-28.

Examples 30-33

A series of oxidations experiments was conducted substantially as in Examples 26-28 except that concentrations of palladium, antimony, tin and molybdenum salts charged to the reactor were varied and the 95 wt % aqueous acetic acid solution charged to the reactor with the catalyst metal salts and as supplemental solvent was diluted or replaced with water. Water contents in weight percent based on total solvent charged and results of analyses of the reactor contents in each of these experiments, including metals concentrations in the supernatant liquid from each run determined by inductive coupled plasma analyses ("ICP") are reported in Table 15.

difficulty, selectivity to carboxylic acid derivatives of the para-xylene feed was greater than 50% and selectivity to terephthalic acid was 6%. Oxidations in water with significantly higher conversions to oxidized para-xylene derivatives and selectivities to terephthalic acid are illustrated in the Examples 34-37 below.

Examples 34-37

Semi-continuous para-xylene oxidations were conducted in water using supported and unsupported catalysts in 300 mL titanium Parr reactors linked to two liquid feed systems and outfitted with a Magnadrive stirrer and two parallel water-cooled titanium condensers for receiving overhead gas vented from the reactor. Gas feed to the reactor was controlled by a mass flow controller, the pressure was regulated by a back pressure regulator and vent gases were continuously analyzed for carbon monoxide, carbon dioxide and oxygen by a bank of

TABLE 15

| | Example | | | | |
|---|---|---|---|---|---|
| | Ave. Ex. 26-28 | 30 | 31 | 32 | 33 |
| Water Conc (wt %) | 5 | 10 | 20 | 40 | 100 |
| Product Sel (%) | | | | | |
| TA | 95.17 | 95.08 | 95.04 | 94.93 | 6.43 |
| 4CBA | 2.92 | 2.58 | 2.12 | 2.70 | 13.88 |
| PTOL | 0.58 | 0.57 | 0.92 | 0.57 | 40.74 |
| PTAL | 0.35 | 0.23 | 0.02 | 0.08 | 36.53 |
| Burned pX | 0.99 | 1.53 | 1.90 | 1.72 | 2.42 |
| pX Conversion (mol %) | 87.68 | 90.85 | 81.52 | 98.20 | 8.73 |
| BA (wt %) | 0.0034 | 0.0022 | 0.0023 | 0.0025 | 0.0012 |
| 2,4,'5-tricarboxybiphenyl (wt %) | 0.0094 | 0.0059 | 0.0051 | 0.0052 | 0.3204 |
| TMLA (wt %) | 0.1674 | 0.1998 | 0.2271 | 0.2199 | 0.0045 |
| COx (moles) | 0.039 | 0.175 | 0.203 | 0.222 | 0.013 |
| $O_2$ Consumed (moles) | 0.905 | 1.103 | 1.104 | 1.036 | 0.349 |
| COx/pX (mol/mol) | 0.145 | 0.649 | 0.753 | 0.827 | 0.047 |
| COx/$O_2$ * 100 (mol/mol) | 4.354 | 15.835 | 18.370 | 21.467 | 3.718 |
| Supernatant Metals | | | | | |
| Palladium (ppmw) | | 1138 | 1166 | 1710 | 141 |
| Antimony (ppmw) | | 725 | 774 | 1441 | 1157 |
| Tin (ppmw) | | 567 | 676 | 1300 | 1110 |
| Molybdenum (ppmw) | | 1090 | 1102 | 2640 | 2793 |

These examples and the table illustrate effectiveness of the catalyst composition in oxidations with increasing water contents from 5 to 100 wt %. Of course, at 100%, the solvent is only water. In oxidations using bromine-promoted cobalt-manganese catalyst compositions conventionally used in commercial manufacture of terephthalic acid, and also those using bromine free catalysts as in US Patent Application No. 2002/0188155, even small increases in water content of the liquid phase reaction mixtures can adversely affect both conversions and selectivity to desired terephthalic acid products. Surprisingly, however, Examples 30-32 and Table 15 illustrate that oxidations progressed actively, and with high selectivities to terephthalic acid, at water contents as high as 40 wt %. It also was surprising that selectivities to intermediate oxidation products such as 4CBA, PTAL and PTOL decreased slightly with increases in water concentration to 40 wt %. The decreases in selectivities for these intermediates are indicative of higher catalyst activity in the conversion of the intermediates to terephthalic acid. At 100 wt % water as liquid medium for the oxidation in Example 33, conversion was lower than expected due to ineffective mixing of para-xylene and water in the apparatus used, but even with that three analyzers to continuously monitor the vent gases for concentrations of carbon monoxide, carbon dioxide, and oxygen. The reactor was heated using a heating mantel; the heating profile was managed by a Parr controller.

The catalysts used in Examples 36 and 37 were supported catalyst compositions composed of palladium, antimony and molybdenum loaded at levels reported in TABLE 16 on titania and were prepared by calcining in air at 650° C. a mixed anatase and rutile phase titania powder identified as P25 having average primary particle size of 21 nm and BET surface area of 50 m²/g obtained from Degussa, cooling the titania, and wet impregnating it by excess liquid impregnation at room temperature using an aqueous solution containing palladium nitrate, antimony acetate, and ammonium heptamolybdate which was prepared by mixing individual stock solutions of the salts in relative proportions corresponding to the loading levels of the final supported catalyst compositions. The palladium nitrate stock solution was an aqueous 35 wt % solution of palladium nitrate. The antimony acetate stock solution was prepared by mixing 5 grams antimony acetate with 10 grams citric acid monohydrate and 30 grams water at 60° C. for 1 hour and then cooling to room temperature. The ammonium heptamolybdate stock solution consisted of 10 grams ammonium heptamolybdate that had been mixed in 20 grams citric acid monohydrate and 60 grams water at 60° C. for 1 hour and then allowed to cool to room temperature. After addition of the impregnating solution to the titania, the slurry was homogenized by shaking briefly. The slurry was then dried at 50° C. for 60 hours, heated to 120° C. at a rate of 2° C. per minute, and held at 120° C. for 2 hours. The dried solid was then calcined under flowing air (100 mL/min) by heating slowly (0.4° C./min) to 400° C. and holding at 400° C. for 2 hours under air flow. The calcined solid was ground to a free-flowing powder and transferred to a crucible. The calcined solid was then reduced with hydrogen by exposure to a flow of dilute hydrogen (7 vol % $H_2$ in nitrogen) for 1 hour at room temperature and then heating in an oven to 250° C. with increases in oven temperature at a rate of 0.4° C./min), after which the temperature was held at 250° C. for 5 hours under dilute hydrogen flow.

The carbon-supported palladium used in combination with antimony and molybdenum acetate salt solutions in Examples 34 and 35 was a commercially available carbon-supported palladium in powder form containing 5 wt % palladium and obtained from Aldrich Corporation.

Oxidation runs were begun by charging the reactor bottom with weighed amounts of catalyst or catalyst components and of distilled and deionized water ("D&D Water") as liquid medium for the reaction. In each of these Examples 2.0 g of p-toluic acid were also added to the reaction mixture. After affixing the reactor bottom to the reactor head the reactor was filled and pressurized to 450 psig using high pressure bottled nitrogen. The reactor contents then were stirred and heating to a target initiation temperature, reported in TABLE 16 below, was begun. Once the reactor contents reached the target initiation temperature, reactions were begun by discontinuing the nitrogen flow and beginning a flow of 8 vol % oxygen and 92 vol % nitrogen. Feed of liquid para-xylene at rates as shown in TABLE 16 was then started. Semi-continuous oxidations were conducted for pre-determined periods of time, also as reported in the table, and then the liquid feed addition was stopped but with continuation of the 8% oxygen and 92% nitrogen flow and constant heating for an additional period of time as reported in the table.

After the oxidation periods ended, the 8% oxygen plus 92% nitrogen flow was stopped and nitrogen flow was resumed at 15 SCFH. The heating mantel was shut off and the reactor and its contents were allowed to cool to room temperature. At that point, the reactor was depressurized, the reactor bottom was detached and a sample of the total reactor effluent was collected for analysis by HPLC. Reaction conditions and results are shown in TABLE 16. Feedstock conversions in the table do not take into account unreacted feedstock that entered the vapor phase in the reactor such that it was no longer available for conversion to aromatic products. Unreacted feedstock entering the vapor phase was estimated to be not more than about 5 wt % by weight of the feed material.

TABLE 16

| | Example No. | | | |
|---|---|---|---|---|
| | 34 | 35 | 36 | 37 |
| Reactor Charge | | | | |
| 5% Pd/2.5% Sb/ 5% Mo/Titania (g) | — | — | 4.5051 | — |
| 5% Pd/5% Sb/ 2.5% Mo/Titania (g) | — | — | — | 7.5 g |
| 5% Pd/Carbon (g) | 5.8503 | 5.8514 | — | — |
| Pd (II) acetate (g) | — | — | — | — |
| Sb (III) acetate (g) | 0.5209 | 0.5230 | — | — |
| Sn (II) acetate (g) | — | — | — | — |
| Mo (II) acetate dimer (g) | 0.6510 | 0.6258 | — | — |
| D&D water (g) | 139.4 | 135.2 | 134.1 | 150.7 |
| pX added (g) | 20.14 | 22.36 | 22.36 | 21.70 |
| p-Toluic Acid (g) | 2.0 | 2.0 | 2.0 | 2.00 |
| Feedstock Conversion (mol %) | 90.3 | 100 | 100 | 98.3 |
| Oxidation Conditions | | | | |
| Initiation Temp. (° C.) | 200 | 210 | 210 | 210 |
| Oxidation Temp. (° C.) | 205 | 210 | 210 | 210 |
| Oxidation Time (min) | 90 | 90 | 90 | 90 |
| Tailout Time (min) | 15 | 15 | 15 | 15 |
| 8% Oxygen Flow (SCFH) | 9 | 9 | 9 | 9 |
| Reactor Pressure (psig) | 455 | 455 | 455 | 390 |
| Product Selectivity (%) | | | | |
| TA | 94.30 | 90.85 | 85.37 | 92.43 |
| 4CBA | 0.92 | 0.60 | 6.69 | 1.11 |
| PTOL | 1.65 | 0.64 | 3.88 | 2.23 |
| PTAL | 0.14 | 0.26 | <0.01 | 0.18 |
| Burned pX | 2.99 | 5.20 | 4.01 | 1.18 |
| By-products (wt % of Total Product) | | | | |
| BA | 0.2236 | 2.44 | 0.04 | 2.89 |
| TMA | <0.0001 | N/A | N/A | NA |
| $CO_2/CO$ (mol/mol) | >50 | >50 | >50 | >50 |

Example 38

Following the procedure of Examples 1-2, a series of para-xylene oxidation trials in aqueous acetic acid solvent at different temperatures was conducted using compositions prepared from various combinations of palladium(II) acetate, antimony(III) acetate, tin(II) acetate and acetic acid-soluble salts of one or more of additional metal or metalloid or standardized solutions thereof in aqueous acetic acid in amounts providing the metals or metalloids in parts by weight of the acetic acid solvent used in the oxidations as indicated in TABLE 17A. Entries C1 and C2 in the table are Control 1 and Control 2, which are included for reference. Examples 1 and 2 are also included for reference.

TABLE 17A

| No. | Pd/Sb | Mo | Ti | Cr | V | Ca | Ni | Ce | Hf |
|---|---|---|---|---|---|---|---|---|---|
| Ex. 1 | 483/505 (494 Sn) | — | — | — | — | — | — | — | — |
| 38-1 | 499/483 | — | 515 | — | — | — | — | — | — |
| 38-2 | 477/492 | — | 508 | — | — | — | — | — | — |
| Ex. 2 | 511/495 (489 Sn) | — | — | — | — | — | — | — | — |
| 38-3 | 474/471 | 465 | — | — | 458 | — | — | — | — |
| 38-4 | 467/467 | 461 | — | — | — | 490 | — | — | — |
| 38-5 | 526/469 | — | — | — | 456 | — | 469 | — | — |
| 38-6 | 489/517 | — | — | 455 | 462 | — | — | — | — |
| 38-7 | 507/479 | 519 | — | 481 | — | — | — | — | — |
| 38-8 | 464/467 | — | — | — | — | — | — | 457 | 456 |
| C2 | 511/0 (504 Sn) | — | — | — | — | — | — | — | — |
| 38-9 | 507/524 | — | — | — | — | — | — | 487 | 493 |
| C1 | 504.7/513.2 | — | — | — | — | — | — | — | — |
| 38-10 | 504/499 | — | — | — | 458 | — | — | — | 458 |
| 38-11 | 486/533 | — | — | — | 458 | 474 | — | — | — |
| 38-12 | 486/515 | — | — | — | — | 486 | 482 | — | — |
| 38-13 | 461/467 | 468 | — | — | — | — | 466 | — | — |
| 38-14 | 449/497 | — | — | — | — | 482 | — | 449 | — |
| 38-15 | 507/473 | — | — | 503 | — | — | — | 499 | — |
| 38-16 | 495/474 | — | — | — | — | — | 466 | — | 492 |
| 38-17 | 464/467 | 513 | — | — | — | — | — | 461 | — |
| 38-18 | 526.0/501.4 | — | — | — | — | — | — | — | 499.7 |

| | Pd/Sn | Mo | Sb | Cr | V | Ca | Ni | Ce | Hf |
|---|---|---|---|---|---|---|---|---|---|
| 38-19 | 464/470 | 461 | 462 | — | — | — | — | — | — |
| 38-20 | 464/520 | — | 531 | — | 460 | — | — | — | — |
| 38-21 | 483/498 | — | 494 | 451 | — | — | — | — | — |
| 38-22 | 507/479 | 519 | — | 481 | — | — | — | — | — |

Results of oxidations with the compositions according to TABLE 10 A are reported in TABLE 17 B.

TABLE 17B

| Example or Trial # | Composition | Temp. (° C.) | Conversion (mole %) | Selectivity (%) | | |
|---|---|---|---|---|---|---|
| | | | | TA | 4CBA | PTOL |
| Ex. 1 | Pd/Sb/Sn | 168 | 94.67 | 2.70 | 3.67 | 77.58 |
| 38-1 | Pd/Sb/Ti | 170 | 89.41 | 1.03 | 2.45 | 84.23 |
| 38-2 | Pd/Sb/Ti | 166 | 78.11 | 2.93 | 3.68 | 89.83 |
| Ex. 2 | Pd/Sb/Sn | 147 | 78.98 | 4.04 | 4.25 | 72.04 |
| 38-3 | Pd/Sb/Mo/V | 175 | 57.71 | 0.44 | 2.43 | 58.22 |
| 38-4 | Pd/Sb/Mo/Ca | 173 | 55.46 | 0.79 | 2.18 | 81.72 |
| 38-5 | Pd/Sb/V/Ni | 171 | 49.15 | 0.86 | 2.58 | 66.05 |
| 38-6 | Pd/Sb/Cr/V | 171 | 46.16 | 0.99 | 2.42 | 71.79 |
| 38-7 | Pd/Sn/Mo/Cr | 172 | 25.30 | 13.90 | 5.35 | 65.83 |
| 38-8 | Pd/Sb/Ce/Hf | 171 | 23.87 | 0.00 | 0.61 | 83.78 |
| C2 | Pd/Sn | 169 | 10.88 | 6.13 | 6.24 | 65.60 |
| 38-9 | Pd/Sb/Ce/Hf | 174 | 9.81 | 0.00 | 0.55 | 83.50 |
| C1 | Pd/Sb | 167 | 8.20 | 0.00 | 0.47 | 76.75 |
| 38-10 | Pd/Sb/V/Hf | 167 | 6.42 | 0.00 | 0.00 | 18.27 |
| 38-11 | Pd/Sb/V/Ca | 175 | 6.40 | 0.00 | 0.30 | 35.50 |
| 38-12 | Pd/Sb/Ca/Ni | 166 | 0.49 | 0.00 | 0.00 | 0.00 |
| 38-13 | Pd/Sb/Mo/Ni | 171 | 0.38 | 0.00 | 0.00 | 0.00 |
| 38-14 | Pd/Sb/Ca/Ce | 174 | 0.22 | 0.00 | 0.00 | 0.00 |
| 3815 | Pd/Sb/Cr/Ce | 173 | 0.17 | 0.00 | 0.00 | 0.00 |
| 38-16 | Pd/Sb/Ni/Hf | 172 | 0.13 | 0.00 | 0.00 | 0.00 |
| 38-17 | Pd/Sb/Mo/Ce | 171 | 0.13 | 0.00 | 0.00 | 0.00 |
| 38-18 | Pd/Sb/Hf | 165 | 0.11 | 0.00 | 0.00 | 0.00 |
| 38-19 | Pd/Sn/Sb/Mo | 170 | 90.89 | 0.74 | 3.14 | 66.97 |
| 38-20 | Pd/Sn/Sb/V | 170 | 59.56 | 1.80 | 3.01 | 73.79 |
| 38-21 | Pd/Sn/Sb/Cr | 170 | 63.18 | 1.13 | 2.77 | 80.08 |
| 38-22 | Pd/Sn/Mo/Cr | 172 | 25.30 | 13.90 | 5.35 | 65.83 |

We claim:

1. A process for conversion of an aromatic feedstock comprising a substituted aromatic hydrocarbon having at least one oxidizable substituent group to an oxidized aromatic product comprising at least one aromatic carboxylic acid comprising contacting the aromatic feedstock with oxygen in a liquid reaction mixture in the presence of a catalyst composition having activity for such conversion in the absence of bromine comprising (A) palladium, (B) a Group 15 metal or metalloid selected from antimony, bismuth and combinations thereof and (C) at least one Group 4, 5, 6 or 14 metal or metalloid.

2. The process of claim 1 wherein the catalyst composition comprises at least one Group 5 metal.

3. The process of claim 1 wherein the catalyst composition comprises at least one Group 6 metal.

4. The process of claim 1 wherein the catalyst composition comprises antimony.

5. The process of claim 1 wherein the catalyst composition comprises at least one of titanium, vanadium, chromium, molybdenum and tin.

6. The process of claim 5 wherein the catalyst composition comprises molybdenum.

7. The process of claim 5 wherein the catalyst composition comprises tin.

8. The process of claim 1 wherein the catalyst composition comprises gold.

9. The process of claim 1 wherein the liquid reaction mixture comprises at least one $C_{1-8}$ monocarboxylic acid solvent for the aromatic feedstock.

10. The process of claim 1 wherein the liquid reaction mixture comprises water and no more than about 10 wt. % $C_{1-8}$ monocarboxylic acid.

11. The process of claim 1 wherein at least a portion of the catalyst composition is soluble in the liquid reaction mixture.

12. The process of claim 1 wherein at least a portion of the catalyst composition is insoluble in the liquid reaction mixture.

13. The process of claim 1 wherein at least a portion of the catalyst composition is carried on a support material.

14. The process of claim 1 wherein carbon monoxide and carbon dioxide are generated in the process in an amount less than about 0.1 mole per mole of oxygen consumed.

15. The process of claim 1 wherein the liquid reaction mixture is free of reactive bromine.

16. The process of claim 1 wherein the substituted aromatic compound is a dialkylarene or a partially oxidized dialkylarene derivative or a combination thereof.

17. The process of claim 16 wherein the substituted aromatic compound is para-xylene or a partially oxidized para-xylene derivative or a combination thereof.

18. The process of claim 16 wherein the oxidized aromatic product comprises terephthalic acid, p-toluic acid, 4-carboxybenzaldehyde, hydroxymethyl benzoic acid or a combination thereof.

19. The process of claim 16 wherein the substituted aromatic compound is meta-xylene or a partially oxidized meta-xylene derivative or a combination thereof.

\* \* \* \* \*